United States Patent
Machielsen et al.

(10) Patent No.: US 10,731,186 B2
(45) Date of Patent: Aug. 4, 2020

(54) GENETICALLY MODIFIED (R)-LACTIC ACID PRODUCING THERMOPHILIC BACTERIA

(71) Applicant: PURAC BIOCHEM BV, Gorinchem (NL)

(72) Inventors: Marinus Petrus Machielsen, Gorinchem (NL); Mariska Van Hartskamp, Gorinchem (NL); Richard Van Kranenburg, Gorinchem (NL)

(73) Assignee: PURAC BIOCHEM BV, Gorinchem (NL)

(*) Notice: Subject to any disclaimer, the term of this patent is extended or adjusted under 35 U.S.C. 154(b) by 387 days.

(21) Appl. No.: 15/327,495

(22) PCT Filed: Jul. 13, 2015

(86) PCT No.: PCT/EP2015/065990
§ 371 (c)(1),
(2) Date: Jan. 19, 2017

(87) PCT Pub. No.: WO2016/012296
PCT Pub. Date: Jan. 28, 2016

(65) Prior Publication Data
US 2017/0275656 A1    Sep. 28, 2017

(30) Foreign Application Priority Data

Jul. 23, 2014  (EP) .................................... 14178144

(51) Int. Cl.
| | | |
|---|---|---|
| C12P 7/56 | (2006.01) | |
| C12N 9/04 | (2006.01) | |
| C07K 14/195 | (2006.01) | |
| C12N 9/10 | (2006.01) | |
| C12N 9/88 | (2006.01) | |
| C12N 15/52 | (2006.01) | |
| C12N 15/74 | (2006.01) | |

(52) U.S. Cl.
CPC ............ *C12P 7/56* (2013.01); *C07K 14/195* (2013.01); *C12N 9/0006* (2013.01); *C12N 9/1029* (2013.01); *C12N 9/88* (2013.01); *C12N 15/52* (2013.01); *C12N 15/74* (2013.01); *C12Y 101/01027* (2013.01); *C12Y 101/01028* (2013.01); *C12Y 203/01008* (2013.01); *C12Y 203/01054* (2013.01); *C12Y 402/03003* (2013.01)

(58) Field of Classification Search
None
See application file for complete search history.

(56) References Cited

U.S. PATENT DOCUMENTS

| | | | |
|---|---|---|---|
| 2004/0024879 A1 | 2/2004 | Dingman et al. | |
| 2005/0106694 A1 | 5/2005 | Green et al. | |
| 2007/0037265 A1* | 2/2007 | Zhou .................. | C12N 1/20 435/139 |

FOREIGN PATENT DOCUMENTS

| | | |
|---|---|---|
| EP | 2843039 A1 | 3/2015 |
| JP | 2003-47490 A | 2/2003 |
| JP | 2006-527589 A | 12/2006 |
| JP | 2007-49993 A | 3/2007 |
| JP | 2009-536017 A | 10/2009 |
| JP | 2014-500018 A | 1/2014 |
| WO | 2004/113510 A2 | 12/2004 |
| WO | 2005/086670 A2 | 9/2005 |
| WO | WO 2005-086670 A2 * | 9/2005 |
| WO | 2007/085443 A2 | 8/2007 |
| WO | 2007/120198 A2 | 10/2007 |
| WO | 2012/071392 A2 | 5/2012 |
| WO | 2013/162274 A1 | 10/2013 |
| WO | 2014/017469 A1 | 1/2014 |

OTHER PUBLICATIONS

Kovacs et al. Genetic Tool Development for a New Host for Biotechnology, the Thermotolerant Bacterium *Bacillus coagulans*. Applied and Environmental Microbiology, Jun. 2010, vol. 76, No. 12, p. 4085-4088.*
Cripps et al. Metabolic engineering of Geobacillus thermoglucosidasius for high yield ethanol production. Metabolic Engineering, vol. 11 (2009), 398-408.*
Feb. 13, 2018 Office Action and Search Report issued in Canadian Patent Application No. 2,955,717.
Jan. 9, 2019 Office Action issued in Chinese Patent Application No. 201580040167.3.
Wesley Loftie-Eaton et al., "Balancing Redox Cofactor Generation and ATP Synthesis: Key Microaerobic Responses in Thermophilic Fermentations," Biotechnology and Bioengineering, vol. 110, Issue 4, Apr. 2013, pp. 1057-1065.
Translation of May 3, 2018 Office Action issued in Korean Patent Application No. 10-2017-7001921.
"D-lactate dehydrogenase [Lactobacillus delbrueckii].", GenBank: AAA25246.1.

(Continued)

*Primary Examiner* — Iqbal H Chowdhury
(74) *Attorney, Agent, or Firm* — Oliff PLC

(57) ABSTRACT

The invention relates to a genetically engineered thermophilic bacterial cell that is facultative anaerobic comprising: a) inactivation or deletion of the endogenous (S)-lactate dehydrogenase gene; b) introduction of a (R)-lactate dehydrogenase gene; c) inactivation or deletion of the endogenous pyruvate formate lyase A and/or B gene.

17 Claims, No Drawings

Specification includes a Sequence Listing.

(56) References Cited

OTHER PUBLICATIONS

Dong-Eun Chang et. al., "Homofermentative Production of D- or L-Lactate in Metabolically Enigneered *Escherichia coli* RR1", Applied and Enivommental Microbiology, vol. 65 (4), p. 1384-1389, 1999.
Gonzy-Tréboul, et al., "Developmental regulation of transcription of the bacillus subtilis ftsAZ operon." J. Mol. Biol., vol. 224:967-979, 1992.
May 8, 2019 Office Action issued in Japanese Patent Application No. 2017-502827.
Jun. 6, 2018 Office Action issued in Japanese Patent Application No. 2017-502827.
Catalanotti, et al. "Altered fermentative metabolism in chlamydomonas reinhardtii mutants lacking pyruvate formate lyase and both pyruvate formate lyase and alcohol dehydrogenase." The plant cell, vol. 24:692-707, 2012.
Van Zyl et al., "Engineering pyruvate decarboxylase-mediated ethanol production in the thermophilic host geobacillus thermoglucosidasius" Appl Microbiol Biotechnol, 98:1247-1259, 2014.
Fong et al., "Isolation and characterization of two novel ethanol-tolerant facultative-anaerobic thermophilic bacteria strains from waste compost." Extremophilies, 10:363-372, 2006.
Beyer, et al., "Coordination of FocA and pyruvate formate-lyase synthesis in *Escherichia coli* demonstrates preferential translocation of formate over other mixed-acid fermentation products." Journal of Bacteriology, vol. 195 No. 7, 1428-1435, 2013.
Thompson et al., "Heterologous expression of pyruvate decarboxylase in geobacillus thermoglucosidasius." Biotechnol Lett vol. 30 No. 8:1359-1365, 2008.
Suzuki, et al., "Production of extracellular a-glucosidase by a thermophilic bacillus species." Applied and environmental microbiology, vol. 31 No. 6: 807-812, 1976.
Liu et al., "Production of lactate in *Escherichia coli* by redox regulation genertically and physiologically." Appl. Biochem biotechnol vol. 164:162-169, 2011.
Cripps et al., "Metabolic engineering of geobacillus thermoglucosidasius for high yield ethanol production." Metabolic engineering.
Zhou, et al., "Functional replacement of the *Escherichia coli* D-(-)-lactate dehydrogenase gene (IdhA) with the L-(+)-lactate dehydrogenase gene (IdhL) from pediococcus acidilactici." Applied and environmental microbiology, vol. 69 No. 4:2237-2244, 2003.
Payton et al.,"Mutants of bacillus stearothermophilus lacking NAD-linked L-lactate dehydrogenase." FEMS Microbiology letters, vol. 26:333-336, 195, 1985.
Suzuki et al.,"*Bacillus thermoglucosidasius* sp. No., a new species of obligately thermophilic bacilli." System. Appl. Microbiol, vol. 4:487-495, 1983.

Zhu et al,. "Effect of a single-gene knockout on the metabolic regulation in *Escherichia coli* for D-laclate production under microaerobic condition." Metabolic engineering, vol. 7:104-115, 2005.
Tang, et al., "Analysis of metabolic pathways and fluxes in a newly discovered thermophilic and ethanol-tolerant geobacillus strain." Biotechnology and bioengineering, 2008.
Chandrangsu et al., "Methylglyoxal resistance in bacillus subtilis: contributions of bacillithiol-dependent and independent pathways." Molecular Microbiology, vol. 91(4):706-715, 2014.
Wang et al., "Development of an asporogenic bacillus licheniformis for the production of keratinase," Journal of applied microbiology, vol. 98 No. 98:761-767, 2005.
Helmann, John D. "Bacillithiol, a new player in bacterial redox homeostasis." Antioxidants & redox signaling, vol. 15 No. 1:123-133, 2011.
Kovács, et al., "Genetic tool development for a new host for biotechnology, the thermotolerant bacterium bacillus coagulans." Applied and environmental microbiology, vol. 76 No. 12:4085-4088, 2010.
Gaballa, et al., "Biosynthesis and functions of bacillithiol, a major low-molecular-weight thiol in bacilli." Department of microbiology, vol. 107 No. 14:6482-6486, 2010.
Fleming et al., "Extracellular enzyme synthesis in a sporulation-deficient strain of bacillus lichenifomis." Applied and environmental microbiology, vol. 61 No. 11:3775-3780, 1995.
Grabar et al., "Methylglyoxal bypass identified as source of chiral contamination in L(+) and D(−)-lactate fermentations by recombinant *Escherichia coli*." Biotechnol Lett, 2006.
Coorevits et al., "Taxonomic revision of the genus *Geobacillus*: emendation of Geobacillus, G. stearothermophilus, G. jurassicus, G. toebii, G. thermodenitrificans and G. thermoglucosidans (nom. corrig., formerly 'thermoglucosidasius'); transfer of Bacillus thermantarcticus to the genus as G. thermantarcticus comb. No., proposal of *Caldibacillus debilis* gen. nov., comb. nov.; transfer of G. tepidamans to Anoxybacillus as A. tepidamans comb. nov.; transfer of G. tepidamans comb. nov.; and proposal of *Anoxybacillus caldiproteolyticus* sp. nov.." International journal of systematic and evolutionary microbiology, vol. 62:1470-1485, 2012.
Nazina, et al., "Taxonomic study of aerobic thermophilic bacilli: descriptions of *Geobacillus subterraneus* gen. No., sp. nov. and *Geobacillus uzenensis* sp. nov. from petroleum reservoirs and transfer of Bacillus stearothermophilus, Bacillus thermocatenulatus, bacillus thermoleovorans, bacillus kaustophilus, bacillus thermoglucosidasius and bacillus thermodenitrificans to geobacillus as the new combinations G. stearothermophilus, G. thermocatenulatus, G. thermolevorans, G. thermoglucodasius and G. thermodentrificans." International journal of systematic and evolutionary microbiology, vol. 51:443-446,2001.

\* cited by examiner

GENETICALLY MODIFIED (R)-LACTIC ACID PRODUCING THERMOPHILIC BACTERIA

The present invention relates to modifying a thermophilic bacterial cell for homolactic and enantiopure (R)-lactic acid production, a genetically modified cell, and a method to produce enantiomeric pure (R)-lactic acid.

Lactic acid and its salts, known as lactate, are commercially viable products useful in various fields including medicine, biodegradable polymers and food processing. Thermophilic bacteria, such as *Geobacillus* species, that are facultative anaerobic seem ideal organisms for the industrial manufacture of lactic acid. They are capable of growing at temperatures between 37-75° C., with an optimum at 55-65° C. (Nazina et al., 2001, Int. J. Syst. Evol. Microbiol. 51:433-446) and allow anaerobic industrial fermentation at temperatures above 50° C. This high temperature has several advantages when fermenting on industrial scale: less risk of infections and thus higher enantiomeric purity, faster reactions, lower cooling costs, etcetera. The facultative anaerobic nature of the Geobacilli allows fermentation under anaerobic conditions, or at least under a low partial pressure of oxygen, which for Industrial scale is desirable because it allows for relatively inexpensive equipment and processing. Furthermore, the nutrient requirements of these bacteria are less demanding than those of lactic acid bacteria such as *Lactobacillus* species which also allows for relatively inexpensive industrial processes.

*Geobacillus* species that are facultative anaerobic are known to produce lactic acid when grown under anaerobic conditions, or at least under a low partial pressure of oxygen. Examples are *G. caldotenax, G. caldoxylosilyticus, G. debilis, G. kaustophilus, G. pallidus, G. stearothermophilus, G. tepidimans, G. thermodenitrificans, G. thermoglucosidans, G. thermoleovorans, G. toebii, G. tropicalis.*

*G. thermoglucosidans* is known to produce lactic acid from xylose, arabinose, glucose, fructose, sucrose and cellobiose (Green et al., 2003, WO03/008601). For industrial applications feedstocks containing sucrose, glucose, xylose, or arabinose, or mixtures thereof, are most relevant. The ability to simultaneously utilize glucose and xylose (Green et al., 2003, WO03/008601) is an important advantage of *G. thermoglucosidans* when using fermentable sugars derived from lignocellulosic feedstocks.

One disadvantage of the known *Geobacillus* species that are facultative anaerobic is the fact that they produce mainly (S)-lactic acid and very little (R)-lactic acid. Since successful application of biodegradable lactic acid polymers will depend on the availability of both inexpensive (S)-lactic acid and inexpensive (R)-lactic acid, a cost-effective production of both enantiomers is required. Presently known (R)-lactic acid-producing bacteria are either mesophilic (e.g. *Bacillus laevolacticus*) or have demanding nutrient requirements (e.g. *Lactobacillus delbrueckii*), which makes the manufacture of (R)-lactic acid much more expensive than that of (S)-lactic acid.

Another disadvantage of the known *Geobacillus* species which are facultative anaerobic is the fact that they generally have a mixed acid fermentation, producing lactic acid, ethanol, acetic acid, and formic acid as main fermentation products. In this application the term organic acids is meant to also include their corresponding salts.

There is a clear need to be able to use bacterial strains (e.g. *Geobacillus* strains) for homolactic and enantiopure lactic acid production that have attractive characteristics for industrial application, such as low nutrient needs, broad sugar consumption capabilities, the capacity to produce carbohydrolytic enzymes, high growth rate, high productivity, resistance to osmotic stress, and genetic accessibility.

One of the objects of the present invention is to produce a thermophilic bacterial strain which is facultative anaerobic and produces (R)-lactic acid by homolactic fermentation. It is to be understood that other terms for (R)-lactic acid are D-lactic acid or D(−)-lactic acid. In this application these terms are interchangeably used. Similarly, the terms (S)-lactic acid, L-lactic acid and L(+)-lactic acid are interchangeably used.

Another object of the present invention is to produce a thermophilic bacterial strain which is facultative anaerobic and produces enantiopure (R)-lactic acid.

*G. thermoglucosidans* is described as a thermophilic *Bacillus* species (Suzuki et al., 1983, Syst. Appl. Microbiol. 4:487-495; Nazina et al., 2001, Int. J. Syst. Evol. Microbiol. 51:433-446; Coorevits et al., 2012, Int. Syst. Evol. Microbiol. 62:14770-1485). *G. thermoglucosidans* was previously known as *Bacillus thermoglucosidasius* (Suzuki et al., 1983, Syst. Appl. Microbiol. 4:487-495), which was renamed to *G. thermoglucosidasius* by Nazina et al. in 2001 (Nazina et al., 2001, Int. J. Syst. Evol. Microbiol. 51:433-446), and later renamed to *G. thermoglucosidans* by Coorevits et al. (Coorevits et al., 2012, Int. Syst. Evol. Microbiol. 62:14770-1485). The type strain was isolated from soil (Suzuki et al., 1976, Appl. Environ. Microbiol. 31:807-812). Although originally reported as strictly aerobic, later studies report facultative anaerobic growth and (S)-lactic acid production (Green et al., 2003, WO 03/008601; Fong et al., 2006, Extremophiles 10:363-372). Temperature range is between 42 and 69° C., with an optimum of 62° C. (Suzuki et al., 1983, Syst. Appl. Microbiol. 4:487-495). Genetic modification of *G. thermoglucosidans* strains for ethanol production has been reported (Green et al., 2001, WO 01/49865; Atkinson et al., 2008, WO08/038019). This includes description of the genetic tools for *G. thermoglucosidans* DSM 2542$^T$ and a method to disrupt the L-lactate dehydrogenase (ldh) gene (Atkinson et al., 2006, WO2006/117536 and 2008, WO2008/038019). Metabolic pathways and fluxes for cells grown on xylose and glucose have been reported for *G. thermoglucosidans* M10EXG (Tang et al. 2009, Biotechnol. Lett. 102: 1377-1386).

Inactivation of lactate dehydrogenase (ldhL) in *Geobacillus* species has been shown to optimize ethanol production (Payton et al., 1985, FEMS Microbiol. Lett. 26:333-336; Green et al., 2001; Atkinson et al., 2006, WO 2006/117536; Cripps et al., 2009, Metab. Eng. 11:398-408). Cripps et al. show that ldhL$^-$ derivatives of *G. thermoglucosidans* NCIMB 11955 show strong reduction, but not complete elimination of lactic acid production in batch fermentations, while ethanol, formate and pyruvate production is increased. A combined mutation of ldhL and pflB, encoding pyruvate formate lyase, eliminates formate production (Cripps et al., 2009, Metab. Eng. 11:398-408).

Heterologous gene expression appears to be problematic in *G. thermoglucosidans*. A functional enzyme of *Zymomonas mobilis* pyruvate decarboxylase was only produced when grown at 52° C., a suboptimal temperature for *G. thermoglucosidans*, but not at 54° C., 56° C., or 58° C. (Thompson et al., 2008, Biotechnol. Lett. 30:1359-1365). Heterologous expression of the *Gluconobacter oxydans* pyruvate decarboxylase gene requires codon harmonization to get activity in *G. thermoglucosidans* at 45° C., but fails to provide activity at 52° C. (van Zyl et al., 2014, Appl. Microbiol. Biotechnol. 98:1247-1259).

Van Kranenburg et al. show that the moderately thermophilic *Bacillus coagulans* can be used for (R)-lactic acid production at temperatures between 45° C. and 54° C. by deleting the native L-lactate dehydrogenase gene and replacing it with a heterologous D-lactate dehydrogenase gene obtained from *Lactobacillus delbrueckii* (van Kranenburg et al., 2007, WO2007/085443). However, no examples of heterologous proteins active at temperatures above 52° C. can be found in heterologous expression experiments of pyruvate decarboxylase genes in *G. thermoglucosidans*, while the optimum temperature for this species is generally around 60° C. Moreover, it is not known if the D-lactate dehydrogenase from *L. delbrueckii* is active at 60° C.

We have now found that a thermophilic bacterial cell can be used for production of (R)-lactic acid by disrupting the endogenous L-lactate dehydrogenase gene ldhL and introducing a gene encoding D-lactate dehydrogenase activity. We have independently introduced the ldhA gene (SEQ ID NO: 35) and hdhD gene (SEQ ID NO: 37) of a *L. delbrueckii* isolate, both encoding D-lactate dehydrogenase activity. Those skilled in the art know that other genes encoding D-lactate dehydrogenase activity that are functionally expressed in *G. thermoglucosidans* can be used instead.

*Geobacillus* species that are facultative anaerobic show mixed acid fermentations with lactic acid, ethanol, acetic acid, and formic acid as main products. Disruption of genes encoding essential enzymes in production of by-products is a common approach to improve production of a desired product. However, effects of the disruption of a specific gene can have different side-effects depending on the overall metabolism of the host. Single mutations in *Escherichia coli* pflA, encoding pyruvate-formate lyase activating enzyme, and adhE, encoding bifunctional acetaldehyde-CoA/alcohol dehydrogenase complex, result in improved lactic acid production with concomitant increased pyruvate by-product formation, residual acetic acid and ethanol production and strongly reduced biomass yield (pflA⁻) or improved lactic acid production with acetic acid as main fermentation product (adhE⁻) (Zhu & Shimizu, 2005, Metab. Eng. 7:104-115). In several *E. coli* strains the focA-pflAB locus has been disrupted to eliminate formic acid production (Zhou et al., 2003, Appl. Environ. Microbiol. 69:2237-2244; Liu et al., 2011, Appl. Biochem. Biotechnol. 164:162-169). The importance of focA, encoding a formate channel protein, in lactic acid accumulation in the medium was recently shown (Beyer et al., 2013, J. Bacteriol. 195:1428-1435), so it will be contributing to the phenotypes of *E. coli* strains having focA-pflAB deletions. In the green alga *Chlamydomonas reinhardtii* knockouts of genes coding for pyruvate formate lyase and alcohol dehydrogenase improved lactic acid fermentation, but also increased extracellular glycerol and acetate concentrations (Catalanotti et al., 2012, Plant Cell 24:692-707).

In *G. thermoglucosidans* the pflBA genes are convergently oriented to the adhE gene. For practical reasons we decided to disrupt pflA, pflB, and adhE by deleting pflBA and part of adhE in one modification. Surprisingly, we were able to nearly abolish ethanol, acetic acid, and formic acid by-product formation without impacting other by-products and without impacting lactic acid fermentation performance. For instance, in the instant application that the by-product formation is nearly abolished means that by fermenting a genetically engineered cell as described herein the weight amount of by-products (such as ethanol, acetic acid, and formic acid) with respect to the total amount of lactic acid produced is of no more than 10% (w/w), and in particular no more than 5%, 4%, 3% or 2% (w/w). The amount of lactic acid and of by-products can be determined by methods known in the art, e.g. by derivatisation and analysis by gas-liquid chromatography (GLC) or High-performance liquid chromatography (HPLC).

There are several options that can result in chiral impurity in lactic acid production described in literature. (R)-lactic acid can be formed from pyruvate by the activity of a D-lactate dehydrogenase, it can be formed from (S)-lactic acid by the activity of a lactate racemase, or it can be formed through the methylglyoxal pathway. (S)-lactic acid can be formed from pyruvate by the activity of a L-lactate dehydrogenase, it can be formed from (R)-lactic acid by the activity of a lactate racemase, or it can be formed through the methylglyoxal pathway.

Methylglyoxal synthase (E.C. 4.2.99.11) catalyzes the conversion of dihydroxyacetone phosphate to methylglyoxal and orthophosphate in the first step of the methylglyoxal bypass. Next, methylglyoxal can be converted via two different pathways to (S)- or (R)-lactic acid. Therefore, the methylglyoxal bypass could be a source of chiral contamination for production of both (S)- and (R)-lactic acid. In the Gram-negative mesophilic bacterium *Escherichia coli* disruption of the mgsA gene encoding methylglyoxal synthase improved the chiral purity for production of both (S)- and (R)-lactic acid (Grabar et al., 2006, Biotechnol. Lett. 28:1527-1535). In Gram-positives little is known on the activity of the methylglyoxal pathway. In the mesophilic *Bacillus subtilis* the mgsA gene is encoded in an operon together with genes encoding the first two enzymes in bacillithiol biosynthesis (Gaballa et al., 2010, Proc. Natl. Acad. Sci. USA 107:6482-6486; Helmann, 2011, Antioxidants & Redox signaling 15:123-133). Recently, Chandrangsu et al. have demonstrated that bacillithiol is involved in methylglyoxal detoxification (Chandrangsu et al., 2014, Mol. Microbiol. 91:706-715). The bacillithiol-dependent methylglyoxal pathway utilizes glyoxalase I (GlxA) and glyoxalase II (FlxB) to convert methylglyoxal to (R)-lactic acid (Chandrangsu et al., 2014). In addition, methylglyoxal can be converted to (R)-lactic acid by the activity of YdeA, YraA, and YfkM, predicted homologues of glyoxalase III (Chandrangsu et al., 2014, Mol. Microbiol. 91:706-715). There are no reports on production of (S)-lactic acid by the methylglyoxal pathway in Gram-positive bacteria.

Based on the genome information one would expect that the (S)-lactic acid production is not caused by a lactate racemase, for which no homologue is found, nor by the methylglyoxal pathway, which seems incomplete and is not known to produce (S)-lactic acid in Gram-positive organisms. Surprisingly, the minute amount of (S)-lactic acid produced in an (R)-lactic acid-producing *Geobacillus* strain that was modified by disrupting the endogenous L-lactate dehydrogenase gene ldhL and introducing a gene encoding D-lactate dehydrogenase activity, could be further reduced by disrupting the mgsA gene, predicted to encode methylglyoxal synthase.

Sporulation deficiency is a desired property for industrial application of *Bacillus* species. According to Directive 2009/41/EC of the European Parliament and of the Council of 6 May 2009 on the contained use of genetically modified micro-organisms, contained uses of genetically modified micro-organisms should be classified in relation to the risk they present to human health and the environment. Having an sporulation-deficient phenotype for *Bacillus* species is seen as a means to minimize the risk of spreading in the environment. Different methods are known to obtain sporulation-deficient phenotypes, including selecting spontaneous sporulation-deficient derivatives (Green et al., 2001, WO01/

49865) or directed disruption of the sporulation pathway e.g., by disrupting spo0A (Gonzy-Tréboul et al., 1992, J. Mol. Biol. 244:967-979; Atkinson et al., 2010, WO2010/052499) or sigF (Fleming et al., 1995, Appl. Environ. Microbiol. 61:3775-3780; Wang et al., 2005, J. Appl. Microbiol. 98:761-767; Kovacs et al., 2010, Appl. Environ. Microbiol. 76:4085-4088).

Thus, in a first aspect the invention discloses a genetically engineered thermophilic bacterial cell that is facultative anaerobic comprising
a) inactivating or deleting the endogenous (S)-lactate dehydrogenase gene;
b) introduction of a (R)-lactate dehydrogenase gene;
c) inactivation or deletion of the endogenous pyruvate formate lyase A and/or B gene.

Endogenous genes are genes which are present in a microorganism. It goes without saying that a bacterium as described herein wherein a gene is inactivated or deleted requires for the gene to be inherently present in the bacterium. In absence of an indication to the contrary, in the present application any reference to a gene means an endogenous gene. Genes which are introduced into a microorganism, such as a (R)-lactate dehydrogenase gene introduced to bacterial cells as described herein, are not endogenous genes.

In the present specification the nucleotide sequence of (S)-lactate dehydrogenase gene (ldhL) is provided in SEQ ID NO.47 for *Geobacillus thermoglucosidans*. The encoded amino acid sequence is provided in SEQ ID NO. 48:

The nucleotide regions flanking ldhL can be identified by the downstream primers SEQ ID NOs 11 and 12 and the upstream primers SEQ ID NOs 13 and 14 for *Geobacillus thermoglucosidans*.

Suitable genes coding for (R)-lactate dehydrogenase activity are those genes that encode an amino acid sequence of SEQ ID NOs:36 or 38, or homologous genes that encode an amino acid sequence that displays a degree of identity of at least 90%, to the amino acid sequence of SEQ ID NOs: 36 or 38, preferably 95%, more preferably at least 98%, and yet more preferably at least 99% degree of identity. (R)-lactate activity can be demonstrated by overexpression of the gene in a suitable host and subsequent quantification of (R)-lactate enzyme activity in the cell extract by using an enzymatic assay or can be demonstrated by the ability to complement an *E. coli* ldhA⁻ mutant, such as *E. coli* FMJ144. Such homologous sequences may encompass polymorphisms that may exist in cells from different populations or within a population due to natural or intra-strain variation. A homologue may further be derived from species other than the species where the specified DNA or amino acid sequence originates from, or may be artificially designed and synthesized. The proteins identified by SEQ ID NOs:36 and 38 are encoded by the ldhA and hdhD genes of *Lactobacillus delbrueckii*. Both genes encode a D-lactate dehydrogenase activity.

In one embodiment according to the present invention the genetically engineered cell comprises an (R)-lactate dehydrogenase gene which is the hdhD gene from *Lactobacillus delbrueckii* encoding the amino acid sequence of SEQ ID NO:38 or an amino acid sequence having at least 90%, preferably 95% identity, more preferably at least 98%, and yet more preferably at least 99% degree of identity.

In another embodiment according to the present invention the genetically engineered cell comprises a (R)-lactate dehydrogenase gene which is the ldhA gene from *Lactobacillus delbrueckii* encoding the amino acid sequence of SEQ ID NO:36 or an amino acid sequence having at least 90%, preferably 95% identity, more preferably at least 98%, and yet more preferably at least 99%.

In yet another embodiment the hdhD gene in the cell according to the invention encodes the amino acid sequence of SEQ ID NO:38.

In another embodiment the ldhA gene in the cell according to the invention encodes the amino acid sequence of SEQ ID NO:36.

In another embodiment according to the present invention the genetically engineered cell comprises the hdhD gene according to the nucleotide sequence of SEQ ID NO:37.

In again another embodiment the genetically engineered cell comprises the ldhA gene according to the nucleotide sequence in SEQ ID NO:35.

In a preferred embodiment the endogenous pyruvate-formate lyase gene is inactivated by inactivation or deletion of the pyruvate-formate lyase/alcohol dehydrogenase locus pflBA-adhE. Alternatively, the endogenous pyruavate lyase A and/or B gene and the endogenous alcohol dehydrogenase genes adhE can be inactivated or deleted in separate steps. The the nucleotide regions flanking pflBA-adhE can be identified by the PCR primers of SEQ ID NOs 19-21.

In the present specification with pflBA is meant the pyruvate-formate lyase genes A and B, encoding pyruvate-formate lyase activating enzyme and pyruvate formate lyase, respectively.

plfA refers to the pyruvate formate lyase A gene (encoding pyruvate-formate lyase activating enzyme) the sequence of which is provided in SEQ ID NO:39 for *Geobacillus thermoglucosidans*. The encoded amino acid sequence is provided in SEQ ID NO:40. plfB refers to the pyruvate formate lyase B gene (encoding pyruvate formate lyase) the nucleotide sequence of which is provided in SEQ ID NO:41. The encoded amino acid sequence is provided in SEQ ID NO:42. In the present invention adhE refers to the alcohol dehydrogenase gene E, encoding bifunctional acetaldehyde-CoA/alcohol dehydrogenase complex, the nucleotide sequence of which is provided in SEQ ID NO:43 for *Geobacillus thermoglucosidans*. The encoded amino acid sequence is provided in SEQ ID NO:44.

In a preferred embodiment inactivation by the pyruvate-formate lyase gene is inactivated by inactivation or deletion of the pyruvate-formate lyase/alcohol dehydrogenase locus pflBA-adhE. Alternatively, the pyruavate lyase A and/or B gene and the alcohol dehydrogenase genes adhE can be inactivated or deleted in separate steps.

In the present invention the nucleotide regions flanking adhE can be identified by the PCR primers SEQ ID NOs 9 and 10 for *Geobacillus thermoglucosidans*.

In another embodiment according to the present invention in the genetically engineered cell also the endogenous methylglyoxal synthase gene (mgsA) is inactivated or deleted.

In the present specification the nucleotide regions flanking mgsA can be identified by the PCR primers SEQ ID NOs: 21-24 for *Geobacillus thermoglucosidans*.

The nucleotide sequence of mgsA is provided in SEQ ID NO:45 for *Geobacillus thermoglucosidans*. The encoded amino acid sequence is provided in SEQ ID NO:46.

In yet another embodiment according to the present invention in the genetically engineered cell also the phosphotransacetylase gene (pta) is inactivated or deleted. The nucleotide sequence of pta is provided in SEQ ID NO. 49 for *Geobacillus thermoglucosidans*. The encoded amino acid sequence is provided in SEQ ID NO. 50. Inactivation or deletion of pta (which encodes phosphotransacetylase) further minimizes the remnant acetate production associated to endogenous pta activity. The resulting strain (with inactivated or deleted pta) is auxotrophic for acetic acid. Accordingly, when fermenting this genetically engineerd cell acetic acid which has to be supplemented to the growth medium.

In yet another embodiment according to the present invention the genetically engineered thermophilic bacterial cell in addition is made sporulation-deficient by inactivation or deletion of an endogenous sporulation gene.

In another embodiment the inactivated or deleted sporulation gene is sigF.

sigF refers to a sporulation gene the nucleotide sequence of which is provided in SEQ ID NO: 51 for *Geobacillus thermoglucosidans*. The encoded amino acid sequence is provided in SEQ ID NO: 52. The nucleotide sequences flanking sigF can be identified by PCR primers SEQ ID NOs 3-6.

In yet another embodiment the genetically engineered thermophilic bacterial cell according to present invention is a gram positive bacterial cell. Preferably the cell belongs to the genus *Bacillus*, more preferably *Geobacillus*.

In again another embodiment the genetically engineered thermophilic bacterial cell according to present invention is *Geobacillus thermoglucosidans*.

One of the objects of the present invention is to produce a *Geobacillus* strain which is facultative anaerobic and produces (R)-lactic acid by homolactic fermentation.

Thus, in one aspect, the present invention discloses a method for genetic modification of moderately thermophilic *Geobacillus* species that are facultative anaerobic and homolactic by means of genetic engineering.

In the present invention homolactic fermentation is defined by producing lactic acid from hydrocarbon sources with the formation of no more than 15% (w/w), preferably no more than 10% (w/w), and more preferably no more than 5%, 4%, 3% or 2% (w/w) of by-products such as formic acid, acetic acid and ethanol. This percentage relates to the total weight of byproducts over the total weight of lactic acid (including (R)-lactic acid and any (S)-lactic acid that may be present). The amount of lactic acid and ethanol, acetic acid, and formic acid can be determined by methods known in the art, e.g. by derivatisation and analysis by gas-liquid chromatography (GLC) or High-performance liquid chromatography (HPLC).

In several embodiments, the formed amount of at least one of formic acid, ethanol and acetic acid is no more than 5% (w/w), based on the total weight of formic acid, ethanol or acetic acid over the total weight of lactic acid produced, in particular no more than 2%, 1%, 0.25% or 0.1% (w/w). In other words, the weight amount of formic acid formed in the homolactic fermentation may be, e.g., of no more than 5% (w/w) and more in particular no more than 2%, 1%, 0.25% or 0.1% (w/w) relative to the total weight amount of lactic acid. Similarly the weight amount of ethanol may be of no more than 5%, 2%, 1%, 0.25% or 0.1% (w/w) and the amount of acetic acid may be of no more than 5%, 2%, 1%, 0.25% or 0.1% (w/w).

Chiral purity is an important aspect for production of poly-lactic acid polymers. Therefore, it is essential to produce enantiopure (R)-lactic acid for commercial applications.

Thus, the present invention also provides a genetically engineered thermophilic bacterial cell which produces (R)-lactic acid with an enantiomeric purity of at least 98%, more preferably at least 99.5%, 99.8% or 99.9%.

In one aspect of the invention there is provided a method to produce enantiomeric pure lactic acid. The method comprises the steps of: culturing a thermophilic bacterial cell according to the present invention using suitable fermentable carbon containing feedstock and isolating the (R)-lactic acid.

In another aspect the invention provides a method to produce enantiomeric pure lactic acid wherein the carbon containing feedstock comprises xylose, glucose or sucrose.

The temperature of the culturing is preferably performed at a temperature of between 50° C. and 70° C., more preferably between 55 and 65° C.

In the context of the invention, inactivation or deletion of a gene may be modification of a gene encoding a desired polypeptide to be produced by the cell and/or a gene encoding a polypeptide involved in production of a primary or secondary metabolite by the cell. In principle this can be done by decreasing the cellular levels of the encoded protein. Decreasing the cellular levels may be effectuated, example gratia, by targeted inactivation of the gene encoding the enzyme of interest. The gene can be removed in its entirety. However, as an alternative also the deletion of part of the gene might result in a reduction of the activity of the encoded protein. Alternatively, or additionally, nucleotide sequences responsible for the regulation or expression of the genes such as promoters enhancers, translational initiator sites and the like can be modified or removed. Another way to influence the activity of the protein of interest might be the modification of transport signals, if needed, or the introduction of anti-sense RNA.

Chromosomal modification is preferred since chromosomal modification will ensure a stable distribution of the functionality of the gene over the progeny cells. Deletion of a desired functionality in the chromosome can be done with non-homologous as well as with homologous recombination. Homologous recombination is preferred, as it opens the opportunity to introduce, to remove or to simultaneously introduce and remove a functionality.

When homologous recombination is intended, the transforming DNA further contains a DNA sequence that is homologous to a genomic target sequence of the specific cell to be engineered. The skilled person will understand that no 100% identity is required to obtain homologous recombination. A percentage identity of 80%, preferably 90%, 95% or 98% will also suffice. Most preferred is 99%. Generally, the DNA sequence of interest to be inserted in the chromosome by homologous recombination is flanked by homologous sequences with a sufficient length to enable homologous recombination. Such a length may be at least about 200 bp, for instance between about 200 and about 1500 bp, preferably between about 200 and about 1000 bp.

For the purpose of the present invention, the degree of identity between two amino acid sequences refers to the percentage of amino acids that are identical between the two sequences. The degree of identity is determined using the BLAST algorithm, which is described in Altschul, et al., J. Mol. Biol. 215: 403-410 (1990). Software for performing BLAST analyses is publicly available through the National Center for Biotechnology Information. The default settings for Blastp algorithm parameters are Expect threshold of 10, Word size of 3, Max matches in a query range of 0, Matrix is BLOSUM62, Gap Costs Existence of 11 and Extension of 1, Compositional adjustments at Conditional compositional score matrix adjustment.

For the purpose of the present invention, the degree of identity between two nucleotide sequences refers to the percentage of nucleotides that are identical between the two sequences. The degree of identity is determined using the BLAST algorithm, which is described in Altschul, et al., J. Mol. Biol. 215: 403-410 (1990). Software for performing BLAST analyses is publicly available through the National Center for Biotechnology Information. The default settings for Blastn algorithm parameters are Expect threshold of 10, Word size of 28, Max matches in a query range of 0, Match/Mismatch Scores of 1, −2, Gap Costs at Linear.

As mentioned hereinbefore, none of sequences identifying the above genes in *Geobacillus thermoglucosidans* need to be 100% identical in order to modify the gene of interest by genetic engineering. Furthermore, in related thermophilic bacterial cells from other species genes might deviate from these sequences. However, making use of the *Geobacillus thermoglucosidans* gene sequences homologous to these genes and which have the same functionality can easily be identified by those skilled in the art and corresponding primers can be prepared for performing homologous recombination in these strains. Thus, even if deviations from the sequences of the above identified genes exist in a certain strain homologous genes can easily be identified. Its nucleotide sequence can be determined using technologies known in the art and if needed a new set of primers can be defined identical or complementary to the flanking gene sequences.

The cells according to the present invention can be prepared using technologies known in the art. In particular methods to introduce DNA into thermopilic bacteria by electroporation have been described by Van Kranenburg et al., 2007, WO2007/085433 and Cripps et al. 2009, Metab. Eng. 11:398-408.

Transformation of these *Bacillus* species by electroporation can be achieved by a high-voltage discharge through a suspension containing a moderately thermophilic *Bacillus* species that is facultative anaerobic and homolactic and a suitable transforming DNA comprising the desired functionality and/or DNA sequences homologous to genomic sequences of the specific Bacilli.

(R)-Lactic acid can be obtained by fermenting a genetically engineered thermophilic bacterial cell as described herein in the presence of a carbohydrate source (e.g. glucose and/or xylose) by methods known in the art. During fermentation the lactic acid excreted by the micro-organisms is generally neutralized using a base, e.g. basic salts of alkali or alkaline earth metals such as hydroxides, carbonates and/or hydrogen carbonates of sodium, potassium, magnesium, and/or calcium. Magnesium bases, e.g. magnesium hydroxide, magnesium carbonate and/or magnesium hydrogen carbonate, are generally preferred. Accordingly, in several aspects the instant invention particularly relates to a method to produce enantiomeric pure (R)-lactic acid, said method comprising culturing a thermophilic bacterial cell as described herein in the presence of a magnesium base (e.g. selected from at least one of magnesium hydroxide, magnesium carbonate and magnesium hydrogen carbonate) using suitable fermentable carbon containing feedstock and isolating the (R)-lactic acid.

After fermentation, the (R)-lactic acid (or a salt thereof) is separated from the fermentation broth by any of the many conventional techniques known to separate lactic acid and/or lactate from aqueous solutions. Particles of substrate or microorganisms (the biomass) may be removed before separation to enhance separation efficiency. Said separation may be conducted by means of centrifuging, filtration, flocculation, flotation or membrane filtration. This is for instance known from WO 01/38283 wherein a continuous process for the preparation of lactic acid by means of fermentation is described. While the discussion of the fermentation in this specification generally refers to a batch process, parts or all of the entire process may be performed continuously.

After separation of the (R)-lactic acid (or a salt thereof) from the fermentation broth, the product may be subjected to one or more purification steps such as extraction, distillation, crystallization, electrodialysis, filtration, treatment with activated carbon ion exchange, etcetera. The various residual streams may be recycled, optionally after treatment, to the fermentation vessel or to any previously performed purification step.

EXAMPLES

Materials and Methods
Strains and Plasmids

Strains and plasmids used in this study are listed in Table 1.

*Escherichia coli* was routinely cultured in LB broth (Sambrook & Russell, 2001, Molecular Cloning, a laboratory manual. 3rd edition. Cold Spring Harbor Laboratory Press, New York) at 37° C. under aerobic conditions. When appropriate chloramphenicol and/or ampicillin were used at concentrations of 20 mg/L and 100 mg/L, respectively.

*L. lactis* was routinely cultured in M17 Broth® (BD Biosciences) supplemented with 0.5% glucose at 30° C. under anaerobic conditions. When appropriate chloramphenicol was used at a concentration of 5 mg/L.

*G. thermoglucosidans* was routinely grown in TGP medium at 52° C., 55° C. or 60° C. under aerobic conditions, unless stated otherwise. TGP medium (Taylor et al., 2008, Plasmid 60:45-52) contained 17 g/L trypton, 3 g/L soy peptone, 5 g/L NaCl, 2.5 g/L $K_2HPO_4$ at pH 7.0, and post-autoclave additions of 4 ml/L glycerol and 4 g/L Na-pyruvate. For TGP plates 10 g/L agar was used. When appropriate, the medium was supplemented with chloramphenicol (8 μg/mL).

TABLE 1

| Strains and plasmids used in this study | | |
|---|---|---|
| Strain or plasmid | Relevant characteristics | Source or reference |
| Strains | | |
| *E. coli* TG90 | Plasmid-free strain | Gonzy-Tréboul, G., Karmzyn-Campelli, C., Stragier, P. 1992. J. Mol. Biol. 224: 967-979 |
| *E. coli* DH5α | Plasmid-free strain | ZymoResearch |
| *L. lactis* MG1363 | Plasmid-free strain | Gasson, M. J. 1983. J. Bacteriol. 154: 1-9 |

TABLE 1-continued

Strains and plasmids used in this study

| Strain or plasmid | Relevant characteristics | Source or reference |
|---|---|---|
| G. thermoglucosidans DSM 2542 | G. thermoglucosidans type strain | DSMZ, Braunschweig |
| G. thermoglucosidans DSM 2542 ΔsigF | Sporulation-deficient G. thermoglucosidans | This work |
| G. thermoglucosidans DSM 2542 ΔsigF, ΔldhL::hdhD | Sporulation-deficient, (R)-lactic acid producing G. thermoglucosidans | This work |
| G. thermoglucosidans DSM 2542 ΔsigF, ΔldhL::hdhD, ΔpflBA-ΔadhE | Sporulation-deficient, chiral pure, and homolactic (R)-lactic acid producing G. thermoglucosidans | This work |
| G. thermoglucosidans DSM 2542 ΔsigF, ΔldhL::hdhD, ΔpflBA-ΔadhE, ΔmgsA | Sporulation-deficient, chiral pure, and homolactic (R)-lactic acid producing G. thermoglucosidans | This work |
| G. thermoglucosidans DSM 2542 ΔsigF, ΔldhL::ldhA, ΔpflBA-ΔadhE | Sporulation-deficient, homolactic (R)-lactic acid producing G. thermoglucosidans | This work |
| G. thermoglucosidans DSM 2542 ΔsigF, ΔldhL::ldhA, ΔpflBA-ΔadhE, ΔmgsA | Sporulation-deficient, chiral pure, and homolactic (R)-lactic acid producing G. thermoglucosidans | This work |
| Plasmids | | |
| pNW33N | 4.2 kb, $Cm^R$, E. coli/Geobacillus shuttle vector | Bacillus Genetic Stock Centre |
| pNZ124 | 2.8 kb, $Cm^R$, E. coli/Gram-positive shuttle vector | Platteeuw, C., G. Simons, and W. M. de Vos. 1994. Appl. Environ. Microbiol. 60: 587-593 |
| pRM3 | 6.2 kb, $Cm^R$, pNW33n derivative with the upstream and downstream regions of G. thermoglucosidans sigF | This work |
| pRM12 | 6.4 kb, $Cm^R$, pNW33n derivative with upstream and downstream regions of G. thermoglucosidans pflBA-adhE locus | This work |
| pJS65 | 6.3 kb, $Cm^R$, pNZ124 derivative with L. delbrueckii ldhA flanked by upstream and downstream regions of G. thermoglucosidans ldhL | This work |
| pFS3 | 7.9 kb, $Cm^R$, pNW33n derivative with L. delbrueckii hdhD flanked by upstream and downstream regions of G. thermoglucosidans ldhL | This work |
| pJS43 | 6.4 kb, $Cm^R$, pNW33n derivative with upstream and downstream regions of G. thermoglucosidans mgsA | This work |

DNA Manipulation Techniques

Standard DNA manipulation techniques were performed as described by Sambrook and Russell (Sambrook & Russell, 2001, Molecular Cloning, a laboratory manual. 3rd edition. Cold Spring Harbor Laboratory Press, New York).

Construction pNW33N derivatives was performed in E. coli.

Large-scale E. coli plasmid DNA isolation from 100 mL culture was performed using the Jetstar 2.0 Plasmid Maxiprep Kit® (Genomed) following the instructions of the manufacturer. Small-scale E. coli plasmid DNA isolation from 1 mL culture was performed using the Nucleospin Plasmid Quick Pure® (Macherey-Nagel) kit following the instructions of the manufacturer.

E. coli competent cells were prepared using calcium chloride and transformed by heat shock as described by Sambrook and Russell (Sambrook & Russell, 2001, Molecular Cloning, a laboratory manual. 3rd edition. Cold Spring Harbor Laboratory Press, New York).

Construction of pNZ124 derivatives was performed in L. lactis.

L. lactis plasmid DNA isolation from 100 mL culture was performed using the Jetstar 2.0 Plasmid Maxiprep Kit® (Genomed). The cell pellet was resuspended in 10 ml modified E1 buffer (10 mM Tris/HCL pH8; 50 mM NaCl; 10 mM EDTA; 20% sucrose; 4 g/L lysozyme (Sigma Aldrich)) and incubated at 50° C. for 1 hour. Subsequently, the instructions of the manufacturer were followed from cell lysis onwards.

L. lactis was transformed by electroporation as described by Holo and Nes (Holo, H., and I. F. Nes. 1989. Appl. Environ. Microbiol. 55:3119-3123).

PCR reactions for cloning purposes were performed with the high-fidelity Pwo polymerase (Roche) following the instructions of the manufacturer.

For colony-PCR analysis colonies were picked with a tooth pick and a little cell material was transferred to a PCR reaction tube. The cells were disrupted by 1 min incubation at 1000 W in a microwave oven. PCR reaction mixtures of 25 μL with DreamTaq™ DNA Polymerase (Thermo Scientific™) were prepared as recommended by the manufacturer and added to the reaction tubes with the disrupted cells.

Electroporation of G. thermoglucosidans

G. thermoglucosidans was transformed by electroporation, based on the protocol described by Cripps et al. (Cripps, et al., 2009, Metab. Eng. 11:398-408). G. thermoglucosidans was grown overnight at 55° C. and 1 mL was used to inoculate 50 ml pre-warmed TGP medium in a 250 ml conical flask with baffles. Cells were incubated at 60° C. (180 rpm) until the $OD_{600}$ was ≈1.0. The flask was cooled on ice for 10 min. and the cells were pelleted by centrifugation (4° C.). Next, the cells were washed four times with ice cold electroporation buffer (0.5 M sorbitol, 0.5 M mannitol, 10% (v/v) glycerol). The volumes of the washing steps were 50 ml, 25 ml, 10 ml, and 10 ml. The final pellet was resuspended in 1.3 ml of ice cold electroporation buffer and 60 μl aliquots of electrocompetent cells were stored at −80° C. or directly used for electroporation.

A 60 μl aliquot of electrocompetent cells (defrosted) was mixed with 1-2 μg plasmid DNA and subsequently transferred to a chilled electroporation cuvet (gap width 0.1 cm). The electroporation conditions using a Bio-Rad gene pulser electroporator were 2.5 kV, 10 pF and 6000. After electroporation the cells were transferred to 1 ml of pre-warmed (52° C.) TGP in a 50 ml plastic tube and recovered at 52° C., 180 rpm for two hours. The recovered cell suspension was pelleted and all but 150 μl supernatant was discarded. The pellet was resuspended in the remaining supernatant. Volumes of 1/10 and 9/10 were plated onto TGP plates containing 8 μg/L chloramphenicol. The plates were incubated at 52° C. for 24-48 hours. Colonies which appeared on the plates were transferred to a fresh TGP plate containing 8 μg/L chloramphenicol and incubated at 55° C. overnight. Those that grew were tested for the presence of the plasmid by colony PCR using primers 1 and 2 (Table 2).

Integration

The Geobacillus-E. coli shuttle vector pNW33n was used as integration vector in G. thermoglucosidans as previously described (Cripps et al., 2009, Metab. Eng. 11:398-408). 20 mL TGP containing 8 μg/mL chloramphenicol was inoculated with transformed strains from a glycerol stock. After overnight growth at 55° C., 180 rpm, appropriate dilutions were plated on TGP plates containing 8 μg/mL chloramphenicol. These plates were then incubated at 68° C. for 24 h. Single colonies were streaked to a fresh plate (incubated at 52° C.) and a colony PCR was conducted on these colonies to identify a colony with a single crossover. The appropriate primer combinations were used to identify single crossovers via the upstream or downstream fragment (Table 2; primer combinations 655-170 and 656-571 for integration of pRM3, primer combinations 744-170 and 808-571 for integration of pRM12, primer combinations 629-170 and 630-571 for integration of pFS3, primer combinations 754-170 and 991-571 for integration of pJS43, respectively). Next, chromosomal DNA of positive colonies was isolated using the Masterpure Gram Positive DNA Purification Kit (Epicentre Biotechnologies) and to confirm the results of the colony PCR, the PCR described above was repeated on the isolated chromosomal DNA. A single crossover via the upstream flanking region and a single crossover via the downstream flanking region were selected for the second recombination step.

To obtain a double crossover, the primary integrants were sub-cultured several times in TGP without chloramphenicol. Appropriate dilutions ($10^{-4}$, $10^{-5}$, $10^{-6}$) were plated on TGP plates. Isolated colonies were transferred to a TGP plate with and one without 8 μg/mL chloramphenicol. Double crossover mutants are chloramphenicol sensitive. PCR analysis using the appropriate primer combinations (Table 2; primer combinations 655-656 for ΔsigF, 744-808 for ΔpflBA-adhE, and 754-991 for ΔmgsA) was used to discriminate wild-type from deletion mutants and to verify the absence of the plasmid. All modifications were confirmed by sequencing of the PCR products.

The Lactococcus cloning vector pNZ124 was used as integration vector in G. thermoglucosidans for ldhA. Freshly prepared G. thermoglucosidans competent cells with relatively high transformation efficiency (at least $10^3$ CFU/μg pNW33n) were transformed with 2 μg of pJS65 plasmid DNA. The transformation plates were incubated 16 hours at 60° C., 8 hours at 68° C. and 20 hours at 55° C. Single colonies were streaked to a fresh plate (incubated at 52° C.) and colony PCR was conducted on these colonies to identify a colony with a single crossover. The appropriate primer combinations were used to identify single crossovers via the upstream or downstream fragment (Table 2; primer combinations 1539-205 and 204-630).

TABLE 2

Primers used in this study

| SEQ ID NO | Primer ID | Sequence (5'-3')[1] |
| --- | --- | --- |
| 1 | 1 | TCGCCTTCTTCTGTGTCATC |
| 2 | 2 | CTGGAGGAGAGCAATGAAAC |
| 3 | 651 | GCGCGGGTACCCAGCAAACCGAGCGGAATCAG |
| 4 | 652 | GCGCGGTCGACGGATGGGTAGGCATCCATTC |
| 5 | 653 | GCGCGGTCGACGTCTCCCTTAGTTACATAACGC |
| 6 | 654 | GCGCGAAGCTTGCTTCGCAGTCCAATCGTCGC |
| 7 | 739 | GCGCGGGATCCCCCAAATGGCATTACCGGTGTG |
| 8 | 805 | TGTTATTGCTGGCAGTTTCCCTCCCATGCATCTG |
| 9 | 806 | GGAGGGAAACTGCCAGCAATAACACCAACAGGCTC |
| 10 | 807 | GCGCGCTGCAGCGAAAGCGAACGAAATTGCCAAC |
| 11 | 624 | GCGCGGTCGACCTGACTTTGAATACAACAAGGTGAAC |
| 12 | 631 | GCGCGGCATGCCGGCAAACAGAGCTTTAAAACCAGGC |
| 13 | 1200 | CCCGCATGCTTAGCCAACCTTAACTGGAGTTTCAG |
| 14 | 676 | TTTAGTCATCGCTGTCTGTCATCCTTTCC |
| 15 | 675 | GATGACAGACAGCGATGACTAAAATTTTTGCTTACGCAATTCG |
| 16 | 564 | GCGCGGTCGACTTAGCCAACCTTAACTGGAGTTTCAG |
| 17 | 1057 | GCGCGGGATCCCTCGTTGTATTTGGGCATACGTCG |
| 18 | 1203 | CTGACATTATACATGGCAATTTTAGTCATCGCTGT |

TABLE 2-continued

Primers used in this study

| SEQ ID NO | Primer ID | Sequence (5'-3')[1] |
|---|---|---|
| | | CTGTCATCCTTTCC |
| 19 | 1202 | GGAAAGGATGACAGACAGCGATGACTAAAATTGCCATGTATAATGTCAG |
| 20 | 1189 | CGGCTCGAGTTACAGGTTAACGATGCTTCTTGGC |
| 21 | 750 | GCGCGGGATCCGCTTTCCGTTTGCCATTTGCCG |
| 22 | 999 | TATGCGACGGGCGCGTGGAGGAATATTGTCCGC |
| 23 | 1000 | ATTCCTCCACGCGCCCGTCGCATACAGTTCATGTTG |
| 24 | 753 | GCGCGCTGCAGGGCAAGACTGACAGAAGAGCTTGG |
| 25 | 170 | GCCCTCGAGAGGGCTCGCCTTTGGGAAG |
| 26 | 571 | GCTCGTTATAGTCGATCGGTTC |
| 27 | 655 | GCTAAGATCGGCCATACGTTAAGC |
| 28 | 656 | GGAGACGAGCTTGGCGTCCTG |
| 29 | 744 | GCCAAGATGGATATGGGCGTTAGC |
| 30 | 808 | CCGGAGATGGACGGAATTGAAG |
| 31 | 629 | GACTGGGCGCAAGCGGTGATG |
| 32 | 630 | CCTGTTGCTGATACAAGGTCTAGC |
| 33 | 754 | CAGCAGTAACGGCATCCGATTG |
| 34 | 991 | GCGGATATGATTGAATTTGTGACTGCC |
| 53 | 204 | CTGCAAGCTTTGGCAGACAACGGCATCAC |
| 54 | 205 | TTGCGTAACCGAAGACCTTGCCTGAGTCC |
| 55 | 957 | CCTCGAGCGGCAAACAGAGCTTTAAAACCAGGC |
| 56 | 1537 | GGGTCTAGAGCCGCTTCGTTTTCCAACTGATGC |
| 57 | 1539 | TCTTTCGCTTCCAGGGCTGTTC |
| 58 | 1589 | GCGCGGAGCTCGTCGACCTGACTTTGAATACAACAAGGTGAAC |

[1]Restriction sites are underlined

Fermentation

TMM medium was modified from Fong et al. (Fong et al., 2006) and contained per L: 60 g/L glucose; 30 g/L xylose; 8.37 g MOPS, 0.23 g $K_2HPO_4$; 0.51 g $NH_4Cl$; 0.50 g NaCl; 1.47 g $Na_2SO_4$; 0.08 g $NaHCO_3$; 0.25 g KCl; 1.87 g $MgCl_2.6H_2O$; 0.41 g $CaCl_2.2H_2O$; 16.0 mg $MnCl_2.4H_2O$; 1.0 mg $ZnSO_4.7H_2O$; 2.0 mg $H_3BO_3$; 0.1 mg $CuSO_4.5H_2O$; 0.1 mg $Na_2MoO_4.2H_2O$; 1.0 mg $CoCl_2.6H_2O$; 7.0 mg $FeSO_4.7H_2O$; 0.1 mg thiamine; 0.1 mg riboflavin; 0.5 mg nicotinic acid; 0.1 mg panthothenic acid; 0.5 mg pyridoxamine, HCl; 0.5 mg pyridoxal, HCl; 0.1 mg D-biotin; 0.1 mg folic acid; 0.1 mg p-aminobenzoic acid; 0.1 mg cobalamin. pH was adjusted to pH 7.2. Glucose, xylose, metals and vitamins were filter sterilized. Medium was autoclaved. TMM1, TMM2.5, and TMMS were supplemented with 1 g/L, 2.5 g/L, and 5 g/L yeast extract (Oxoid), respectively. STMM, differed from TMM in concentrations of $K_2HPO_4$ (1.00 g/L), $NH_4Cl$ (2.50 g/L), NaCl (5.00 g/L), and $CaCl_2.2H_2O$ (50 mg/L) and was supplemented with D,L-methionine (68.5 mg/L) and betaine (0.14 g/L). Sucrose (90 g/L) was used instead of glucose and xylose. STMM5 was supplemented with 5 g/L yeast extract (Biospringer).

A 100 mL preculture in TMMS or STMM5 was used to inoculate (10% v/v) 400 mL TMM1, TMM2.5, or STMM5 in a 0.75 L Multifors fermentor (Infors) equipped with a condenser (cooled with running tap water of approximately 15° C.). The pH was controlled at pH 7.2 by addition of sterile 2.5 M KOH or sterile 75 g/L $Ca(OH)_2$. Temperature was 60° C. Stirrer speed was 300 rpm Samples were withdrawn from the fermentation for measurement of (R)- and (S)-lactic acid, and possible by-products. Samples were centrifuged and remaining debris was removed by filtration using a Millex GP 0.22 μm Filter® (Millipore). Filtrate was stored at −21° C. until further analysis.

Sugars were measured by HPLC using a Thermo CarboPac SA-10 column (Dionex). Formic acid was measured by HPLC using a Bio-Rad Aminex HPX-87C column (Bio-Rad). Other organic acids (lactic acid, acetic acid, succinic acid, fumaric acid, pyruvic acid) and ethanol were measured using a derivatisation and gas-liquid chromatography (GLC). (R)- and (S)-lactates were methylated to methyl-lactate and measured by headspace analysis on a chiral column.

Example 1

Homolactic Lactic Acid Production with *G. thermoglucosidans*

Integration plasmid pRM3 was constructed to delete the sigF gene in *G. thermoglucosidans*. The upstream and downstream flanking regions of the sigF gene were generated by PCR using genomic DNA of DSM 2542 as template and primer combinations 653 and 654 (Table 2) to obtain the upstream fragment, and the primers 651 and 652 (Table 2) to obtain the downstream fragment. First, the downstream fragment was cloned as KpnI-SalI fragment into pNW33n, digested with the same enzymes. Next, the upstream fragment was cloned as SalI-HindIII fragment into this construct, digested with the same enzymes resulting in plasmid pRM3. Construction of pRM3 was done in *E. coli* TG90. The integrity of the pRM3 sequence was confirmed by DNA sequencing.

Plasmid pRM3 was electroporated to *G. thermoglucosidans* DSM 2542. A single transformant colony was selected and used to obtain single crossover mutants as described in Materials and Methods. Two colonies were selected for further work, one with a single crossover via the upstream flanking region and one with a single crossover via the downstream flanking region.

A double crossover mutant was obtained following the procedure described in Materials and Methods. Sixty colonies, obtained after subculturing of the single crossover integrants in TGP without chloramphenicol, were transferred to TGP plates with and without chloramphenicol. Fifteen colonies were sensitive to chloramphenicol. Twelve colonies had the desired modification and three had reverted to wild-type. One colony was selected and designated *G. thermoglucosidans* DSM 2542 ΔsigF. The deletion was confirmed by sequencing.

TABLE 3

Fermentations with *G. thermoglucosidans* DSM 2542 ΔsigF a glucose/xylose mixture on TMM2.5.

| Time (h) | Glucose (g/L) | Xylose (g/L) | Total lactic acid (g/kg) | Chiral purity (S)-lactic acid (%) | Acetic acid (g/kg) | Formic acid (g/kg) | Ethanol (g/kg) |
|---|---|---|---|---|---|---|---|
| 24 | 18.5 | 11.4 | 29 | 89.5 | <0.1 | 1.2 | 2.2 |
| 48 | 15.2 | 7.0 | 33 | 89.4 | <0.1 | 1.2 | 2.2 |

*G. thermoglucosidans* DSM 2542 ΔsigF was evaluated in pH-controlled (KOH) fermentation using TMM2.5. Fermentations were transferred 4 times and the final fermentations were analysed. The results are summarized in Table 3. *G. thermoglucosidans* DSM 2542 ΔsigF consumed xylose and glucose simultaneously.

Example 2

Construction of (R)-Lactic Acid-Producing *G. thermoglucosidans* Derivative Using hdhD.

Plasmid pFS3 was constructed to facilitate the gene replacement of the native ldhL gene with the hdhD gene originating from *L. delbrueckii* and encoding D-lactate dehydrogenase activity. Construction was such that hdhD start and stop codons replace the positions of the original ldhL start and stop codons and result in a translational fusion of hdhD to the ldhL promoter. The downstream flanking region of the ldhL gene was generated by PCR using genomic DNA of DSM 2542 as template and primer combination 624 and 631. The product was digested with SalI and SphI and ligated into pNW33n digested with SalI and SphI. The resulting plasmid was designated pFS2. Construction of pFS2 was done in *E. coli* DH5a.

The upstream flanking region of the ldhL gene was generated by PCR using genomic DNA of DSM 2542 as template and primer combination 1057 and 1203. The hdhD gene (SEQ ID NO: 37) was generated by PCR using *L. delbrueckii* genomic DNA as template and primer combination 1202 and 1189. The gene can also be synthesized based on SEQ ID NO: 37. The resulting two PCR-products are subsequently used as template in an overlap-PCR using primer combination 1057 and 1189 to fuse them together. The product was digested with BamHI and XhoI and ligated in pFS2 digested with BamHI and SalI. The resulting plasmid was designated pFS3. Construction of pFS3 was done in *E. coli* TG90. Integrity of the pFS3 nucleotide sequence was confirmed by sequencing.

Plasmid pFS3 was electroporated to *G. thermoglucosidans* DSM 2542 ΔsigF. A single transformant colony was selected and used to obtain single crossover mutants as described in Materials and Methods. In the number of colonies tested only single crossover mutants via the downstream flanking region were obtained. One of these was selected for further work.

A double crossover mutant was obtained following the procedure described in Materials and Methods. Colonies, obtained after subculturing of the single crossover integrant in TGP without chloramphenicol, were transferred to TGP plates with and without chloramphenicol. Seventeen colonies sensitive to chloramphenicol were checked by PCR. One colony had the desired modification and 16 had reverted to wild-type. The colony having ldhL exchanged by hdhD was selected and designated *G. thermoglucosidans* DSM 2542 ΔsigF, ΔldhL::hdhD.

To further optimize *G. thermoglucosidans* DSM 2542 ΔsigF, ΔldhL::hdhD there was a wish to eliminate formic acid, acetic acid, and ethanol byproduct formation. Although mutations of pflA and/or pflB and adhE are known to impact formic acid and ethanol production in many bacteria, the side effects of disrupting those genes are unpredictable.

In order to evaluate the effect of the disruption of these genes, a plasmid (pRM12) was constructed to delete the genes pflB, pflA and adhE (partially) in *G. thermoglucosidans*. The upstream flanking region of pflBA and the upstream flanking region of the convergently oriented adhE were generated by PCR using genomic DNA of DSM 2542 as template and primer combinations 739 and 805 to obtain the upstream pflBA fragment and the primers 806 and 807 to acquire the upstream adhE fragment. The resulting two PCR-products were subsequently used as template in an overlap-PCR using primer combination 739 and 807 to fuse them together. The product was cloned as BamHI-PstI fragment into plasmid pNW33n digested with BamHI and PstI, resulting in plasmid pRM12. Construction of pRM12 was done in *E. coli* TG90. Integrity of the pRM12 nucleotide sequence was confirmed by sequencing.

Plasmid pRM12 was electroporated to *G. thermoglucosidans* DSM 2542 ΔsigF, ΔldhL::hdhD. A single transformant colony was selected and used to obtain single crossover mutants as described in Materials and Methods. Two colonies were selected for further work, one with a single crossover via the upstream pflBA flanking region and one with a single crossover via the upstream adhE flanking region.

A double crossover mutant was obtained following the procedure described in Materials and Methods. 120 colonies, obtained after subculturing of the single crossover integrants in TGP without chloramphenicol, were transferred to TGP plates with and without chloramphenicol. Five colonies sensitive to chloramphenicol were checked by PCR. Two colonies had the desired modification and three had reverted to wild-type. One colony with the desired modification was selected and was designated *G. thermoglucosidans* DSM 2542 ΔsigF, ΔldhL::hdhD, ΔpflBA-ΔadhE.

*G. thermoglucosidans* DSM 2542 ΔsigF, ΔldhL::hdhD, ΔpflBA-ΔadhE was evaluated in pH-controlled ($Ca(OH)_2$) fermentations using STMM5 medium containing 5 g/L yeast extract and 90 g/L sucrose. Fermentations were transferred and the second fermentation was analysed for the production of homolactic (R)-lactic acid. *G. thermoglucosidans* DSM 2542 ΔsigF, ΔldhL::hdhD, ΔpflBA-ΔadhE was able to produce homolactic (R)-lactic acid with a limited amount of ethanol, formic acid, and acetic acid by-products. Thus, introduction of the HdhD D-lactate dehydrogenase in combination with disruption of the pyruvate-formate lyase and alcohol dehydrogenase complex genes results in a homolactic (R)-lactic acid fermentation at 60° C. with a limited amount of ethanol, formic acid, and acetic acid by-products.

Example 3

Construction of (R)-Lactic Acid-Producing *G. thermoglucosidans* Derivative Using ldhA.

Cloning of ldhA genes originating from *Lactobacillus* species in *E. coli* is known to be problematic (Bernard et al., 1991. FEBS Lett. 290:61-64). To circumvent possible cloning issues we decided to use *L. lactis* as intermediate host and pNZ124 as cloning vector. Plasmid pJS65 was constructed to facilitate the gene replacement of the native ldhL gene with the ldhA originating from *L. delbrueckii* and encoding D-lactate dehydrogenase activity.

Construction was such that ldhA start and stop codons replace the positions of the original ldhL start and stop codons and result in a translational fusion of ldhA to the ldhL promoter.

The downstream flanking region of the ldhL gene is generated by PCR using genomic DNA of DSM 2542 as template and primer combination 1589 and 957. The product is digested with SacI and XhoI and ligated into pNZ124 digested with SacI and XhoI. The resulting plasmid is designated pJS64. Construction of pJS64 is done in *L. lactis* MG1363.

The upstream flanking region of the ldhL gene is generated by PCR using genomic DNA of DSM 2542 as template and primer combination 1537 and 676. The ldhA gene (SEQ ID NO: 35) is generated by PCR using *L. delbrueckii* genomic DNA as template and primer combination 675 and 564. The gene can also be synthesized based on SEQ ID NO: 35 taking into account that the synthetic gene should, preferably, be cloned in pNZ124 and in *L. lactis*. The resulting two PCR-products are subsequently used as template in an overlap-PCR using primer combination 1537 and 564 to fuse them together. The product is digested with XbaI and SalI and ligated in pJS64 digested with XbaI and partially digested with SalI. The resulting plasmid is designated pJS65. Construction of pJS65 is done in *L. lactis* MG1363.

Plasmid pJS65 was electroporated to *G. thermoglucosidans* DSM 2542 ΔsigF, ΔldhL::hdhD, ΔpflBA-ΔadhE for direct integration. A single transformant colony was obtained with a single crossover via the upstream ldhL flanking region. Achieving direct integration in the *G. thermoglucosidans* genome required using freshly prepared competent cells with a relatively high transformation efficiency of at least $10^3$ CFU/μg pNW33n.

A double crossover mutant was obtained following the procedure described in Materials and Methods. 240 colonies, obtained after subculturing of the single crossover integrants in TGP without chloramphenicol, were transferred to TGP plates with and without chloramphenicol. Thirteen colonies sensitive to chloramphenicol were checked by PCR. Ten colonies had the desired modification and three had reverted to wild-type. One colony having ldhL exchanged by ldhA was selected and designated *G. thermoglucosidans* DSM 2542 ΔsigF, ΔldhL:ldhA, ΔpflBA-ΔadhE.

TABLE 4

Fermentation with *G. thermoglucosidans* DSM 2542 ΔsigF, ΔldhL::ldhA, ΔpflBA-ΔadhE on STMM5

| Time (h) | Sucrose (g/kg) | Total lactic acid (g/kg) | Chiral purity (R)-lactic acid (%) | Acetic acid (g/kg) | Formic acid (g/kg) | Ethanol (g/kg) |
|---|---|---|---|---|---|---|
| 0 | 72.1 | 3.3 | 98.9 | 0.2 | <0.05 | <0.2 |
| 24 | 22.0 | 36 | 98.9 | 0.4 | <0.05 | <0.2 |
| 48 | 1.6 | 48 | 98.9 | 0.5 | <0.05 | <0.2 |

*G. thermoglucosidans* DSM 2542 ΔsigF, ΔldhL:ldhA, ΔpflBA-ΔadhE was evaluated in pH-controlled ($Ca(OH)_2$) fermentations using STMM5 medium containing 5 g/L yeast extract and 90 g/L sucrose. Fermentations were transferred and the second fermentation was analysed. The results are summarized in Table 4. These data clearly demonstrate that introduction of the LdhA D-lactate dehydrogenase in combination with disruption of the pyruvate-formate lyase and alcohol dehydrogenase complex genes results in a homolactic (R)-lactic acid fermentation with a limited amount of ethanol, formic acid, and acetic acid by-products.

Example 4

Enantiopure Homolactic Acid Production with *G. thermoglucosidans*

Plasmid pJS43 was constructed to delete 267 bp of the mgsA gene (423 bp) in *G. thermoglucosidans*. The upstream and downstream flanking regions of the mgsA gene were generated by PCR using genomic DNA of DSM 2542 as template and primer combinations 750 and 999 to obtain the mgsA downstream fragment, and the primers 1000 and 753 to acquire the upstream mgsA fragment. The resulting two PCR-products were subsequently used as template in an overlap-PCR using primer combination 750 and 753 to fuse them together. The product was cloned as BamHI-PstI fragment into plasmid pNW33n digested with BamHI and PstI, resulting in plasmid pJS43. Construction of pJS43 was done in *E. coli* TG90. Integrity of the pJS43 nucleotide sequence was confirmed by sequencing.

Plasmid pJS43 was electroporated to *G. thermoglucosidans* DSM 2542 ΔsigF, ΔldhL::hdhD, ΔpflBA-ΔadhE. Single transformant colonies were selected and used to obtain single crossover mutants as described in Materials and Methods. Two colonies were selected for further work, one with a single-crossover via the upstream flanking region and one with a single-crossover via the downstream flanking region.

Double crossover mutants were obtained following the procedure described in Materials and Methods. 400 colonies, obtained after subculturing of the single crossover integrants in TGP without chloramphenicol, were transferred to TGP plates with and without chloramphenicol. Of these 213 colonies were sensitive to chloramphenicol. 39 of the chloramphenicol-sensitive colonies were checked by PCR for double crossovers. Eight colonies had the desired modification and 31 had reverted to wild-type. A single colony with the desired modification was selected and designated *G. thermoglucosidans* DSM 2542 ΔsigF, ΔldhL::hdhD, ΔpflBA-ΔadhE, ΔmgsA. The deletion was confirmed by sequencing.

Plasmid pJS43 was electroporated to *G. thermoglucosidans* DSM 2542 ΔsigF, ΔldhL:ldhA, ΔpflBA-ΔadhE. Single transformant colonies were selected and used to obtain single crossover mutants as described in Materials and Methods. Two colonies were selected for further work, both with a single-crossover via the upstream flanking region. Single-crossovers via the downstream flanking region were not obtained.

Double crossover mutants were obtained following the procedure described in Materials and Methods. 240 colonies, obtained after subculturing of the single crossover integrants in TGP without chloramphenicol, were transferred to TGP plates with and without chloramphenicol. 239 colonies were sensitive to chloramphenicol, of which 134 colonies were checked by PCR for double crossovers. One had the desired modification and 133 reverted back to wild-type. The single colony with the desired modification was selected and designated *G. thermoglucosidans* DSM 2542 ΔsigF, ΔldhL:ldhA, ΔpflBA-ΔadhE, ΔmgsA. The deletion was confirmed by sequencing.

TABLE 5

Fermentation with *G. thermoglucosidans* DSM 2542 ΔsigF, ΔldhL::ldhA, ΔpflBA-ΔadhE, ΔmgsA on STMM5

| Time (h) | Sucrose (g/kg) | Total lactic acid (g/kg) | Chiral purity (R)-lactic acid (%) | Acetic acid (g/kg) | Formic acid (g/kg) | Ethanol (g/kg) |
|---|---|---|---|---|---|---|
| 0 | 74.3 | 2.3 | >99.1 | 0.2 | <0.05 | <0.2 |
| 24 | 43.9 | 24 | 99.9 | 0.2 | <0.05 | <0.2 |
| 48 | 28.2 | 32 | 99.8 | 0.3 | <0.05 | <0.2 |

*G. thermoglucosidans* DSM 2542 ΔsigF, ΔldhL:ldhA, ΔpflBA-ΔadhE, ΔmgsA was evaluated in pH-controlled (Ca(OH)$_2$) fermentations using STMM5 medium containing 5 g/L yeast extract and 90 g/L sucrose. Fermentations were transferred and the second fermentation was analysed. The results are summarized in Table 5. Chiral purity of the (R)-lactic acid produced was >99.0% for low concentrations of lactic acid (<5 g/kg) and >99.7 for higher concentrations of lactic acid (>20 g/kg), which is more pure than lactic acid from strains without disruption of mgsA (Table 5). These data clearly show that despite the apparent incompleteness of the methylglyoxal pathway in *G. thermoglucosidans*, disruption of mgsA results in the ability to produce chiral pure (R)-lactic acid resulting in a homolactic and chiral pure (R)-lactic acid fermentation.

The invention claimed is:

1. A genetically engineered thermophilic bacterial cell that is facultative anaerobic, gram positive, and belongs to the genus *Geobacillus*, said bacterial cell comprising:
   a) inactivation or deletion of an endogenous (S)-lactate dehydrogenase gene;
   b) introduction of a (R)-lactate dehydrogenase gene; and
   c) inactivation or deletion of an endogenous pyruvate formate lyase A and/or B gene and an endogenous alcohol dehydrogenase gene;
   wherein the cell produces a heterologous (R)-lactate dehydrogenase enzyme, the enzyme being active at 60° C.

2. The cell of claim 1 wherein in addition an endogenous methylglyoxal synthase gene mgsA is inactivated or deleted.

3. The cell of claim 1 wherein the (R)-lactate dehydrogenase is the hdhD gene from *Lactobacillus delbrueckii* encoding the amino acid sequence of SEQ ID NO:38 or an amino acid sequence having at least 90% identity.

4. The cell of claim 1 wherein the (R)-lactate dehydrogenase is the ldhA gene from *Lactobacillus delbrueckii* encoding the amino acid sequence of SEQ ID NO:36 or an amino acid sequence having at least 90% identity.

5. The cell of claim 3 wherein the hdhD gene encodes the amino acid sequence of SEQ ID NO:38.

6. The cell of claim 4 wherein the ldhA gene encodes the amino acid sequence of SEQ ID NO:36.

7. The cell of claim 1 wherein in addition an endogenous phosphotransacetylase gene (pta) is inactivated or deleted.

8. The cell of claim 1 which is a sporulation deficient derivative due to inactivation or deletion of an endogenous sporulation gene.

9. The cell of claim 8 wherein the sporulation gene is sigF.

10. The cell of claim 1 wherein the pyruvate formate lyase A and/or B gene is inactivated by inactivation or deletion of the endogenous pyruvate formate lyase/alcohol dehydrogenase locus pflBA-adhE.

11. The cell of claim 1 which produces (R)-lactic acid with an enantiomeric purity of at least 98%.

12. The bacterial cell of claim 1 wherein the genes are modified by homologous recombination.

13. A method to produce enantiomeric pure (R)-lactic acid, said method comprising culturing the genetically engineered thermophilic bacterial cell of claim 1 using suitable fermentable carbon containing feedstock and isolating the (R)-lactic acid.

14. The method according to claim 13 wherein the carbon containing feedstock comprises xylose, glucose or sucrose.

15. The method according to claim 13 wherein the culturing is performed at a temperature of between 50° C. and 70° C.

16. The method according to claim 13 wherein no more than 15% (w/w) of by-products are formed, based on the total weight of by-products over the total weight of lactic acid produced.

17. The method according to claim 13 wherein the formed amount of at least one of formic acid, ethanol and acetic acid is no more than 5% (w/w), based on the total weight of formic acid, ethanol or acetic acid over the total weight of lactic acid produced.

* * * * *

```
                        SEQUENCE LISTING

<160> NUMBER OF SEQ ID NOS: 58

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
tcgccttctt ctgtgtcatc                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
ctggaggaga gcaatgaaac                                               20

<210> SEQ ID NO 3
<211> LENGTH: 32
<212> TYPE: DNA
<213> ORGANISM: Artificial Sequence
<220> FEATURE:
<223> OTHER INFORMATION: Synthetic primer

<400> SEQUENCE: 3
gcgcgggtac ccagcaaacc gagcggaatc ag                                 32

<210> SEQ ID NO 4
<211> LENGTH: 31
<212> TYPE: DNA
<213> ORGANISM: Artificial Sequence
<220> FEATURE:
<223> OTHER INFORMATION: Synthetic primer

<400> SEQUENCE: 4
gcgcggtcga cggatgggta ggcatccatt c                                  31

<210> SEQ ID NO 5
<211> LENGTH: 33
<212> TYPE: DNA
<213> ORGANISM: Artificial Sequence
<220> FEATURE:
<223> OTHER INFORMATION: Synthetic primer

<400> SEQUENCE: 5
```
gcgcggtcga cgtctccctt agttacataa cgc                33

<210> SEQ ID NO 6
<211> LENGTH: 32
<212> TYPE: DNA
<213> ORGANISM: Artificial Sequence
<220> FEATURE:
<223> OTHER INFORMATION: Synthetic primer

<400> SEQUENCE: 6
gcgcgaagct tgcttcgcag tccaatcgtc gc                 32

<210> SEQ ID NO 7
<211> LENGTH: 33
<212> TYPE: DNA
<213> ORGANISM: Artificial Sequence
<220> FEATURE:
<223> OTHER INFORMATION: Synthetic primer

<400> SEQUENCE: 7
gcgcgggatc ccccaaatgg cattaccggt gtg                33

<210> SEQ ID NO 8
<211> LENGTH: 34
<212> TYPE: DNA
<213> ORGANISM: Artificial Sequence
<220> FEATURE:
<223> OTHER INFORMATION: Synthetic primer

<400> SEQUENCE: 8
tgttattgct ggcagtttcc ctcccatgca tctg               34

<210> SEQ ID NO 9
<211> LENGTH: 34
<212> TYPE: DNA
<213> ORGANISM: Artificial Sequence
<220> FEATURE:
<223> OTHER INFORMATION: Synthetic primer

<400> SEQUENCE: 9
ggagggaaac tgccagcaat aacaccaaca ggct               34

<210> SEQ ID NO 10
<211> LENGTH: 34
<212> TYPE: DNA
<213> ORGANISM: Artificial Sequence
<220> FEATURE:
<223> OTHER INFORMATION: Synthetic primer

<400> SEQUENCE: 10
gcgcgctgca gcgaaagcga acgaaattgc caac               34

<210> SEQ ID NO 11
<211> LENGTH: 37
<212> TYPE: DNA
<213> ORGANISM: Artificial Sequence
<220> FEATURE:
<223> OTHER INFORMATION: Synthetic primer

<400> SEQUENCE: 11
gcgcggtcga cctgactttg aatacaacaa ggtgaac            37

<210> SEQ ID NO 12
<211> LENGTH: 37
<212> TYPE: DNA
<213> ORGANISM: Artificial Sequence

```
<220> FEATURE:
<223> OTHER INFORMATION: Synthetic primer

<400> SEQUENCE: 12
gcgcggcatg ccggcaaaca gagctttaaa accaggc                          37

<210> SEQ ID NO 13
<211> LENGTH: 35
<212> TYPE: DNA
<213> ORGANISM: Artificial Sequence
<220> FEATURE:
<223> OTHER INFORMATION: Synthetic primer

<400> SEQUENCE: 13
cccgcatgct tagccaacct taactggagt ttcag                            35

<210> SEQ ID NO 14
<211> LENGTH: 29
<212> TYPE: DNA
<213> ORGANISM: Artificial Sequence
<220> FEATURE:
<223> OTHER INFORMATION: Synthetic primer

<400> SEQUENCE: 14
tttagtcatc gctgtctgtc atcctttcc                                   29

<210> SEQ ID NO 15
<211> LENGTH: 43
<212> TYPE: DNA
<213> ORGANISM: Artificial Sequence
<220> FEATURE:
<223> OTHER INFORMATION: Synthetic primer

<400> SEQUENCE: 15
gatgacagac agcgatgact aaaattttg cttacgcaat tcg                    43

<210> SEQ ID NO 16
<211> LENGTH: 37
<212> TYPE: DNA
<213> ORGANISM: Artificial Sequence
<220> FEATURE:
<223> OTHER INFORMATION: Synthetic primer

<400> SEQUENCE: 16
gcgcggtcga cttagccaac cttaactgga gtttcag                          37

<210> SEQ ID NO 17
<211> LENGTH: 35
<212> TYPE: DNA
<213> ORGANISM: Artificial Sequence
<220> FEATURE:
<223> OTHER INFORMATION: Synthetic primer

<400> SEQUENCE: 17
gcgcgggatc cctcgttgta tttgggcata cgtcg                            35

<210> SEQ ID NO 18
<211> LENGTH: 49
<212> TYPE: DNA
<213> ORGANISM: Artificial Sequence
<220> FEATURE:
<223> OTHER INFORMATION: Synthetic primer

<400> SEQUENCE: 18
ctgacattat acatggcaat tttagtcatc gctgtctgtc atcctttcc              49
```

<210> SEQ ID NO 19
<211> LENGTH: 49
<212> TYPE: DNA
<213> ORGANISM: Artificial Sequence
<220> FEATURE:
<223> OTHER INFORMATION: Synthetic primer

<400> SEQUENCE: 19
ggaaaggatg acagacagcg atgactaaaa ttgccatgta taatgtcag        49

<210> SEQ ID NO 20
<211> LENGTH: 34
<212> TYPE: DNA
<213> ORGANISM: Artificial Sequence
<220> FEATURE:
<223> OTHER INFORMATION: Synthetic primer

<400> SEQUENCE: 20
cggctcgagt tacaggttaa cgatgcttct tggc        34

<210> SEQ ID NO 21
<211> LENGTH: 33
<212> TYPE: DNA
<213> ORGANISM: Artificial Sequence
<220> FEATURE:
<223> OTHER INFORMATION: Synthetic primer

<400> SEQUENCE: 21
gcgcgggatc cgctttccgt ttgccatttg ccg        33

<210> SEQ ID NO 22
<211> LENGTH: 33
<212> TYPE: DNA
<213> ORGANISM: Artificial Sequence
<220> FEATURE:
<223> OTHER INFORMATION: Synthetic primer

<400> SEQUENCE: 22
tatgcgacgg gcgcgtggag gaatattgtc cgc        33

<210> SEQ ID NO 23
<211> LENGTH: 36
<212> TYPE: DNA
<213> ORGANISM: Artificial Sequence
<220> FEATURE:
<223> OTHER INFORMATION: Synthetic primer

<400> SEQUENCE: 23
attcctccac gcgcccgtcg catacagttc atgttg        36

<210> SEQ ID NO 24
<211> LENGTH: 35
<212> TYPE: DNA
<213> ORGANISM: Artificial Sequence
<220> FEATURE:
<223> OTHER INFORMATION: Synthetic primer

<400> SEQUENCE: 24
gcgcgctgca gggcaagact gacagaagag cttgg        35

<210> SEQ ID NO 25
<211> LENGTH: 28
<212> TYPE: DNA
<213> ORGANISM: Artificial Sequence
<220> FEATURE:
<223> OTHER INFORMATION: Synthetic primer

<400> SEQUENCE: 25
gccctcgaga gggctcgcct ttgggaag                                                    28

<210> SEQ ID NO 26
<211> LENGTH: 22
<212> TYPE: DNA
<213> ORGANISM: Artificial Sequence
<220> FEATURE:
<223> OTHER INFORMATION: Synthetic primer

<400> SEQUENCE: 26
gctcgttata gtcgatcggt tc                                                          22

<210> SEQ ID NO 27
<211> LENGTH: 24
<212> TYPE: DNA
<213> ORGANISM: Artificial Sequence
<220> FEATURE:
<223> OTHER INFORMATION: Synthetic primer

<400> SEQUENCE: 27
gctaagatcg gccatacgtt aagc                                                        24

<210> SEQ ID NO 28
<211> LENGTH: 21
<212> TYPE: DNA
<213> ORGANISM: Artificial Sequence
<220> FEATURE:
<223> OTHER INFORMATION: Synthetic primer

<400> SEQUENCE: 28
ggagacgagc ttggcgtcct g                                                           21

<210> SEQ ID NO 29
<211> LENGTH: 24
<212> TYPE: DNA
<213> ORGANISM: Artificial Sequence
<220> FEATURE:
<223> OTHER INFORMATION: Synthetic primer

<400> SEQUENCE: 29
gccaagatgg atatgggcgt tagc                                                        24

<210> SEQ ID NO 30
<211> LENGTH: 22
<212> TYPE: DNA
<213> ORGANISM: Artificial Sequence
<220> FEATURE:
<223> OTHER INFORMATION: Synthetic primer

<400> SEQUENCE: 30
ccggagatgg acggaattga ag                                                          22

<210> SEQ ID NO 31
<211> LENGTH: 21
<212> TYPE: DNA
<213> ORGANISM: Artificial Sequence
<220> FEATURE:
<223> OTHER INFORMATION: Synthetic primer

<400> SEQUENCE: 31
gactgggcgc aagcggtgat g                                                           21

<210> SEQ ID NO 32

```
<211> LENGTH: 24
<212> TYPE: DNA
<213> ORGANISM: Artificial Sequence
<220> FEATURE:
<223> OTHER INFORMATION: Synthetic primer

<400> SEQUENCE: 32
cctgttgctg atacaaggtc tagc                                          24

<210> SEQ ID NO 33
<211> LENGTH: 22
<212> TYPE: DNA
<213> ORGANISM: Artificial Sequence
<220> FEATURE:
<223> OTHER INFORMATION: Synthetic primer

<400> SEQUENCE: 33
cagcagtaac ggcatccgat tg                                            22

<210> SEQ ID NO 34
<211> LENGTH: 27
<212> TYPE: DNA
<213> ORGANISM: Artificial Sequence
<220> FEATURE:
<223> OTHER INFORMATION: Synthetic primer

<400> SEQUENCE: 34
gcggatatga ttgaatttgt gactgcc                                       27

<210> SEQ ID NO 35
<211> LENGTH: 1002
<212> TYPE: DNA
<213> ORGANISM: Lactobacillus delbrueckii
<220> FEATURE:
<221> NAME/KEY: CDS
<222> LOCATION: (1)..(1002)

<400> SEQUENCE: 35
```

| | | | | | | | | | | | | | | | | |
|---|---|---|---|---|---|---|---|---|---|---|---|---|---|---|---|---|
| atg | act | aaa | att | ttt | gct | tac | gca | att | cgt | gaa | gat | gaa | aag | cca | ttc | 48 |
| Met | Thr | Lys | Ile | Phe | Ala | Tyr | Ala | Ile | Arg | Glu | Asp | Glu | Lys | Pro | Phe | |
| 1 | | | | 5 | | | | | 10 | | | | | 15 | | |
| ttg | aag | gaa | tgg | gaa | gac | gct | cac | aag | gac | gtc | gaa | gtt | gaa | tac | act | 96 |
| Leu | Lys | Glu | Trp | Glu | Asp | Ala | His | Lys | Asp | Val | Glu | Val | Glu | Tyr | Thr | |
| | | | 20 | | | | | 25 | | | | | 30 | | | |
| gac | aag | ctt | ttg | acc | cca | gaa | act | gct | gct | ttg | gca | aag | ggt | gct | gac | 144 |
| Asp | Lys | Leu | Leu | Thr | Pro | Glu | Thr | Ala | Ala | Leu | Ala | Lys | Gly | Ala | Asp | |
| | | 35 | | | | | 40 | | | | | 45 | | | | |
| ggt | gtt | gtt | gtt | tac | caa | caa | ctt | gac | tac | acc | gct | gaa | act | ctg | caa | 192 |
| Gly | Val | Val | Val | Tyr | Gln | Gln | Leu | Asp | Tyr | Thr | Ala | Glu | Thr | Leu | Gln | |
| | 50 | | | | | 55 | | | | | 60 | | | | | |
| gct | ttg | gca | gac | aac | ggc | atc | act | aag | atg | agc | ctg | cgt | aac | gtt | ggt | 240 |
| Ala | Leu | Ala | Asp | Asn | Gly | Ile | Thr | Lys | Met | Ser | Leu | Arg | Asn | Val | Gly | |
| 65 | | | | | 70 | | | | | 75 | | | | | 80 | |
| gtt | gac | aac | atc | gac | atg | gct | aag | gct | aag | gaa | ctt | ggc | ttc | caa | atc | 288 |
| Val | Asp | Asn | Ile | Asp | Met | Ala | Lys | Ala | Lys | Glu | Leu | Gly | Phe | Gln | Ile | |
| | | | | 85 | | | | | 90 | | | | | 95 | | |
| acc | aac | gtt | cca | gtt | tac | tca | cca | aac | gcc | atc | gca | gaa | cat | gct | gct | 336 |
| Thr | Asn | Val | Pro | Val | Tyr | Ser | Pro | Asn | Ala | Ile | Ala | Glu | His | Ala | Ala | |
| | | | 100 | | | | | 105 | | | | | 110 | | | |
| atc | caa | gct | gcc | cgc | atc | ctg | cgt | caa | gcc | aag | gct | atg | gac | gaa | aag | 384 |
| Ile | Gln | Ala | Ala | Arg | Ile | Leu | Arg | Gln | Ala | Lys | Ala | Met | Asp | Glu | Lys | |
| | | 115 | | | | | 120 | | | | | 125 | | | | |
| gtt | gcc | cgt | cac | gac | ttg | cgt | tgg | gca | cca | act | atc | ggc | cgt | gaa | gtt | 432 |
| Val | Ala | Arg | His | Asp | Leu | Arg | Trp | Ala | Pro | Thr | Ile | Gly | Arg | Glu | Val | |

```
                    130                 135                 140
cgc gac caa gtt gtt ggt gtt gta ggt act ggc cac atc ggt caa gtc      480
Arg Asp Gln Val Val Gly Val Val Gly Thr Gly His Ile Gly Gln Val
145                 150                 155                 160 ttc atg caa atc atg gaa ggc ttc ggc gct aag gtt atc gct tac gac      528
Phe Met Gln Ile Met Glu Gly Phe Gly Ala Lys Val Ile Ala Tyr Asp
                    165                 170                 175 atc ttc cgc aac cca gaa ttg gaa aag aag ggc tac tac gta gac tca      576
Ile Phe Arg Asn Pro Glu Leu Glu Lys Lys Gly Tyr Tyr Val Asp Ser
                180                 185                 190 ctt gac gac ctg tac aag caa gct gac gtt att tcc ctg cac gtt cct      624
Leu Asp Asp Leu Tyr Lys Gln Ala Asp Val Ile Ser Leu His Val Pro
            195                 200                 205 ggc gtt cca gct aac gtt cac atg atc aac gac aag tca atc gct aaa      672
Gly Val Pro Ala Asn Val His Met Ile Asn Asp Lys Ser Ile Ala Lys
        210                 215                 220 atg aag caa gac gta gtt atc gtt aac gta tca cgt ggt tca ttg gtt      720
Met Lys Gln Asp Val Val Ile Val Asn Val Ser Arg Gly Ser Leu Val
225                 230                 235                 240 gac act gac gcg gtt atc cgt ggt ttg gac tca ggc aag gtc ttc ggt      768
Asp Thr Asp Ala Val Ile Arg Gly Leu Asp Ser Gly Lys Val Phe Gly
                    245                 250                 255 tac gca atg gac gtt tac gaa ggt gaa gtt ggc gtc ttc aac gaa gac      816
Tyr Ala Met Asp Val Tyr Glu Gly Glu Val Gly Val Phe Asn Glu Asp
                260                 265                 270 tgg gaa ggc aag gaa ttc cca gac gca cgt tta gct gac ttg atc gct      864
Trp Glu Gly Lys Glu Phe Pro Asp Ala Arg Leu Ala Asp Leu Ile Ala
            275                 280                 285 cgt cca aac gtt ctg gta act cca cac act gct ttc tac act act cac      912
Arg Pro Asn Val Leu Val Thr Pro His Thr Ala Phe Tyr Thr Thr His
        290                 295                 300 gct gtt cgc aac atg gta att aag gcc ttc gac aac aac ctt gca ttg      960
Ala Val Arg Asn Met Val Ile Lys Ala Phe Asp Asn Asn Leu Ala Leu
305                 310                 315                 320 att gaa ggc aag gaa gct gaa act cca gtt aag gtt ggc taa              1002
Ile Glu Gly Lys Glu Ala Glu Thr Pro Val Lys Val Gly
                    325                 330

<210> SEQ ID NO 36
<211> LENGTH: 333
<212> TYPE: PRT
<213> ORGANISM: Lactobacillus delbrueckii

<400> SEQUENCE: 36

Met Thr Lys Ile Phe Ala Tyr Ala Ile Arg Glu Asp Glu Lys Pro Phe
1               5                   10                  15

Leu Lys Glu Trp Glu Asp Ala His Lys Asp Val Glu Val Glu Tyr Thr
            20                  25                  30

Asp Lys Leu Leu Thr Pro Glu Thr Ala Ala Leu Ala Lys Gly Ala Asp
        35                  40                  45

Gly Val Val Val Tyr Gln Gln Leu Asp Tyr Thr Ala Glu Thr Leu Gln
    50                  55                  60

Ala Leu Ala Asp Asn Gly Ile Thr Lys Met Ser Leu Arg Asn Val Gly
65                  70                  75                  80

Val Asp Asn Ile Asp Met Ala Lys Ala Lys Glu Leu Gly Phe Gln Ile
                85                  90                  95

Thr Asn Val Pro Val Tyr Ser Pro Asn Ala Ile Ala Glu His Ala Ala
            100                 105                 110
```

```
Ile Gln Ala Ala Arg Ile Leu Arg Gln Ala Lys Ala Met Asp Glu Lys
            115                 120                 125

Val Ala Arg His Asp Leu Arg Trp Ala Pro Thr Ile Gly Arg Glu Val
        130                 135                 140

Arg Asp Gln Val Val Gly Val Gly Thr Gly His Ile Gly Gln Val
145                 150                 155                 160

Phe Met Gln Ile Met Glu Gly Phe Gly Ala Lys Val Ile Ala Tyr Asp
                165                 170                 175

Ile Phe Arg Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
        195                 200                 205

Gly Val Pro Ala Asn Val His Met Ile Asn Asp Lys Ser Ile Ala Lys
    210                 215                 220

Met Lys Gln Asp Val Val Ile Val Asn Val Ser Arg Gly Ser Leu Val
225                 230                 235                 240

Asp Thr Asp Ala Val Ile Arg Gly Leu Asp Ser Gly Lys Val Phe Gly
                245                 250                 255

Tyr Ala Met Asp Val Tyr Glu Gly Glu Val Gly Val Phe Asn Glu Asp
            260                 265                 270

Trp Glu Gly Lys Glu Phe Pro Asp Ala Arg Leu Ala Asp Leu Ile Ala
        275                 280                 285

Arg Pro Asn Val Leu Val Thr Pro His Thr Ala Phe Tyr Thr Thr His
    290                 295                 300

Ala Val Arg Asn Met Val Ile Lys Ala Phe Asp Asn Asn Leu Ala Leu
305                 310                 315                 320

Ile Glu Gly Lys Glu Ala Glu Thr Pro Val Lys Val Gly
                325                 330

<210> SEQ ID NO 37
<211> LENGTH: 1002
<212> TYPE: DNA
<213> ORGANISM: Lactobacillus delbrueckii
<220> FEATURE:
<221> NAME/KEY: CDS
<222> LOCATION: (1)..(1002)

<400> SEQUENCE: 37 atg act aaa att gcc atg tat aat gtc agc ccg atc gaa gtg cct tac      48
Met Thr Lys Ile Ala Met Tyr Asn Val Ser Pro Ile Glu Val Pro Tyr
1               5                   10                  15 att gaa gac tgg gct aag aaa aac gat gtc gaa att aag acg acc gac      96
Ile Glu Asp Trp Ala Lys Lys Asn Asp Val Glu Ile Lys Thr Thr Asp
                20                  25                  30 cag gcc ttg acc agc gcg act gta gat tta gct gaa ggg tgc agc agc     144
Gln Ala Leu Thr Ser Ala Thr Val Asp Leu Ala Glu Gly Cys Ser Ser
            35                  40                  45 gtt tcc ctt aag cca ctt ggc ccg gtt gac gaa gaa gtt gtt tac caa     192
Val Ser Leu Lys Pro Leu Gly Pro Val Asp Glu Glu Val Val Tyr Gln
        50                  55                  60 aaa ttg agc gaa tac ggg gtc aag tgc atc ggc ctc aga atc gtt ggc     240
Lys Leu Ser Glu Tyr Gly Val Lys Cys Ile Gly Leu Arg Ile Val Gly
65                  70                  75                  80 ttc aac acc atc aac ttc gac tgg acc aag aag tac aac ttg ctg gtc     288
Phe Asn Thr Ile Asn Phe Asp Trp Thr Lys Lys Tyr Asn Leu Leu Val
                85                  90                  95 acc aac gtt ccg gtc tac tcc ccg cgg gcg atc gct gaa atg acg gtt     336
Thr Asn Val Pro Val Tyr Ser Pro Arg Ala Ile Ala Glu Met Thr Val
```

```
acc cag gcc atg tac ctc ctg cgc aag atc ggg gaa ttc cgc tac cgg    384
Thr Gln Ala Met Tyr Leu Leu Arg Lys Ile Gly Glu Phe Arg Tyr Arg
            115                 120                 125 atg gac cat gac cat gac ttt acc tgg cca agt aac ttg atc agc aat    432
Met Asp His Asp His Asp Phe Thr Trp Pro Ser Asn Leu Ile Ser Asn
130                 135                 140 gaa atc tac aac ttg act gtc ggc ttg atc ggg gtc ggt cac atc ggc    480
Glu Ile Tyr Asn Leu Thr Val Gly Leu Ile Gly Val Gly His Ile Gly
145                 150                 155                 160 agc gcc gtg gca gaa atc ttc tca gcc atg ggg gcc aag gtc atc gcc    528
Ser Ala Val Ala Glu Ile Phe Ser Ala Met Gly Ala Lys Val Ile Ala
                165                 170                 175 tat gac gtg gct tac aac ccg gaa ttt gaa cca ttt ttg acc tac acc    576
Tyr Asp Val Ala Tyr Asn Pro Glu Phe Glu Pro Phe Leu Thr Tyr Thr
            180                 185                 190 gac ttt gac acg gtc ttg aaa gaa gct gac atc gtc tcc ctc cac act    624
Asp Phe Asp Thr Val Leu Lys Glu Ala Asp Ile Val Ser Leu His Thr
195                 200                 205 ccc ctc ttt cca tca acg gaa aac atg atc ggg gaa aag cag ctg aag    672
Pro Leu Phe Pro Ser Thr Glu Asn Met Ile Gly Glu Lys Gln Leu Lys
210                 215                 220 aaa atg aag aag tct gcc tac ttg atc aac tgt gcc cgg ggc gaa tta    720
Lys Met Lys Lys Ser Ala Tyr Leu Ile Asn Cys Ala Arg Gly Glu Leu
225                 230                 235                 240 gtc gac act gga gcc ttg atc aag gcc ttg cag gat ggc gaa atc gcc    768
Val Asp Thr Gly Ala Leu Ile Lys Ala Leu Gln Asp Gly Glu Ile Ala
                245                 250                 255 ggt gcc ggc ctg gac act ttg gct ggg gaa tcc agc tac ttt ggc cac    816
Gly Ala Gly Leu Asp Thr Leu Ala Gly Glu Ser Ser Tyr Phe Gly His
            260                 265                 270 act ggc ctg acg gac agc gaa atc cca gaa gac tac aag acc ctg gcc    864
Thr Gly Leu Thr Asp Ser Glu Ile Pro Glu Asp Tyr Lys Thr Leu Ala
        275                 280                 285 aag atg cca aac gtt gtc att act ccg cac tca gcc ttc tac acg gaa    912
Lys Met Pro Asn Val Val Ile Thr Pro His Ser Ala Phe Tyr Thr Glu
290                 295                 300 act tcc atc cgc aac atg gtg cag atc tgc ttg act gac caa ttg acc    960
Thr Ser Ile Arg Asn Met Val Gln Ile Cys Leu Thr Asp Gln Leu Thr
305                 310                 315                 320 atc gcc aag ggc ggc cgg cca aga agc atc gtt aac ctg taa           1002
Ile Ala Lys Gly Gly Arg Pro Arg Ser Ile Val Asn Leu
                325                 330
```

<210> SEQ ID NO 38
<211> LENGTH: 333
<212> TYPE: PRT
<213> ORGANISM: Lactobacillus delbrueckii

<400> SEQUENCE: 38

```
Met Thr Lys Ile Ala Met Tyr Asn Val Ser Pro Ile Glu Val Pro Tyr
1               5                   10                  15

Ile Glu Asp Trp Ala Lys Lys Asn Asp Val Glu Ile Lys Thr Thr Asp
            20                  25                  30

Gln Ala Leu Thr Ser Ala Thr Val Asp Leu Ala Glu Gly Cys Ser Ser
        35                  40                  45

Val Ser Leu Lys Pro Leu Gly Pro Val Asp Glu Glu Val Val Tyr Gln
    50                  55                  60

Lys Leu Ser Glu Tyr Gly Val Lys Cys Ile Gly Leu Arg Ile Val Gly
```

```
                65                  70                  75                  80
            Phe Asn Thr Ile Asn Phe Asp Trp Thr Lys Lys Tyr Asn Leu Leu Val
                            85                  90                  95

Thr Asn Val Pro Val Tyr Ser Pro Arg Ala Ile Ala Glu Met Thr Val
                           100                 105                 110

Thr Gln Ala Met Tyr Leu Leu Arg Lys Ile Gly Glu Phe Arg Tyr Arg
                           115                 120                 125

Met Asp His Asp His Asp Phe Thr Trp Pro Ser Asn Leu Ile Ser Asn
                           130                 135                 140

Glu Ile Tyr Asn Leu Thr Val Gly Leu Ile Gly Val Gly His Ile Gly
            145                 150                 155                 160

Ser Ala Val Ala Glu Ile Phe Ser Ala Met Gly Ala Lys Val Ile Ala
                           165                 170                 175

Tyr Asp Val Ala Tyr Asn Pro Glu Phe Glu Pro Phe Leu Thr Tyr Thr
                           180                 185                 190

Asp Phe Asp Thr Val Leu Lys Glu Ala Asp Ile Val Ser Leu His Thr
                           195                 200                 205

Pro Leu Phe Pro Ser Thr Glu Asn Met Ile Gly Glu Lys Gln Leu Lys
                           210                 215                 220

Lys Met Lys Lys Ser Ala Tyr Leu Ile Asn Cys Ala Arg Gly Glu Leu
            225                 230                 235                 240

Val Asp Thr Gly Ala Leu Ile Lys Ala Leu Gln Asp Gly Glu Ile Ala
                           245                 250                 255

Gly Ala Gly Leu Asp Thr Leu Ala Gly Glu Ser Ser Tyr Phe Gly His
                           260                 265                 270

Thr Gly Leu Thr Asp Ser Glu Ile Pro Glu Asp Tyr Lys Thr Leu Ala
                           275                 280                 285

Lys Met Pro Asn Val Val Ile Thr Pro His Ser Ala Phe Tyr Thr Glu
                           290                 295                 300

Thr Ser Ile Arg Asn Met Val Gln Ile Cys Leu Thr Asp Gln Leu Thr
            305                 310                 315                 320

Ile Ala Lys Gly Gly Arg Pro Arg Ser Ile Val Asn Leu
                           325                 330

<210> SEQ ID NO 39
<211> LENGTH: 750
<212> TYPE: DNA
<213> ORGANISM: Geobacillus thermoglucosidans
<220> FEATURE:
<221> NAME/KEY: CDS
<222> LOCATION: (1)..(750)

<400> SEQUENCE: 39 atg aaa gga ttt att cat tcc atc gaa tca tgc ggc acc gtc gac ggg      48
Met Lys Gly Phe Ile His Ser Ile Glu Ser Cys Gly Thr Val Asp Gly
1               5                   10                  15 ccg ggc ctt cgc tat gtc atc ttt aca caa ggc tgt gtg ctg cgc tgc      96
Pro Gly Leu Arg Tyr Val Ile Phe Thr Gln Gly Cys Val Leu Arg Cys
            20                  25                  30 caa tat tgc cat aac gcc gat acg tgg gaa att gga aaa gga aaa gaa     144
Gln Tyr Cys His Asn Ala Asp Thr Trp Glu Ile Gly Lys Gly Lys Glu
        35                  40                  45 atg act gtg gaa gaa atc atc gat gac gtg aaa aca tac ttg ccg ttt     192
Met Thr Val Glu Glu Ile Ile Asp Asp Val Lys Thr Tyr Leu Pro Phe
    50                  55                  60 atc aac gct tcc aat ggc gga att acc gtc agc ggc gga gag cct ttg     240
Ile Asn Ala Ser Asn Gly Gly Ile Thr Val Ser Gly Gly Glu Pro Leu
65                  70                  75                  80
```

```
          65                  70                  75                  80
tta caa atc gat ttt tta att gaa tta ttt aaa gca tgc aaa aaa ctg       288
Leu Gln Ile Asp Phe Leu Ile Glu Leu Phe Lys Ala Cys Lys Lys Leu
                    85                  90                  95 ggc att cat acc gcg atc gat tca tcg gga gga tgc tac acg acg gaa       336
Gly Ile His Thr Ala Ile Asp Ser Ser Gly Gly Cys Tyr Thr Thr Glu
                100                 105                 110 gca tcg ttc cag caa aaa tta aat gaa tta ctt tcc tat acc gat tta       384
Ala Ser Phe Gln Gln Lys Leu Asn Glu Leu Leu Ser Tyr Thr Asp Leu
            115                 120                 125 att ttg ctt gat tta aaa cat atc gat gag aaa aaa cac cgg aaa ctg       432
Ile Leu Leu Asp Leu Lys His Ile Asp Glu Lys Lys His Arg Lys Leu
        130                 135                 140 aca gga aaa acc aat aaa cat att tta caa ttt gct cag ttt tta tcc       480
Thr Gly Lys Thr Asn Lys His Ile Leu Gln Phe Ala Gln Phe Leu Ser
145                 150                 155                 160 gaa aaa aac gtt cct gtt tgg atc cgg cat gtt ctc gtt cca acc atc       528
Glu Lys Asn Val Pro Val Trp Ile Arg His Val Leu Val Pro Thr Ile
                165                 170                 175 aca gac gac ccg aat gac ttg cgc cgt ctc gcc gct ttt att cgc aca       576
Thr Asp Asp Pro Asn Asp Leu Arg Arg Leu Ala Ala Phe Ile Arg Thr
            180                 185                 190 tta aag aat gtg aaa aaa att gaa att ctc cca tac cat aaa tta gga       624
Leu Lys Asn Val Lys Lys Ile Glu Ile Leu Pro Tyr His Lys Leu Gly
        195                 200                 205 gta tac aaa tgg aaa gcg ctt gga tta aaa tac cct ttg gaa gga atc       672
Val Tyr Lys Trp Lys Ala Leu Gly Leu Lys Tyr Pro Leu Glu Gly Ile
    210                 215                 220 gag cct cct tcg gaa gaa agc gta caa atg gca cag cga att ctt aac       720
Glu Pro Pro Ser Glu Glu Ser Val Gln Met Ala Gln Arg Ile Leu Asn
225                 230                 235                 240 gga aca gaa gat aca gta tct ctt gcg taa                               750
Gly Thr Glu Asp Thr Val Ser Leu Ala
                245

<210> SEQ ID NO 40
<211> LENGTH: 249
<212> TYPE: PRT
<213> ORGANISM: Geobacillus thermoglucosidans

<400> SEQUENCE: 40

Met Lys Gly Phe Ile His Ser Ile Glu Ser Cys Gly Thr Val Asp Gly
1               5                   10                  15

Pro Gly Leu Arg Tyr Val Ile Phe Thr Gln Gly Cys Val Leu Arg Cys
            20                  25                  30

Gln Tyr Cys His Asn Ala Asp Thr Trp Glu Ile Gly Lys Gly Lys Glu
        35                  40                  45

Met Thr Val Glu Glu Ile Ile Asp Asp Val Lys Thr Tyr Leu Pro Phe
    50                  55                  60

Ile Asn Ala Ser Asn Gly Gly Ile Thr Val Ser Gly Gly Glu Pro Leu
65                  70                  75                  80

Leu Gln Ile Asp Phe Leu Ile Glu Leu Phe Lys Ala Cys Lys Lys Leu
                85                  90                  95

Gly Ile His Thr Ala Ile Asp Ser Ser Gly Gly Cys Tyr Thr Thr Glu
            100                 105                 110

Ala Ser Phe Gln Gln Lys Leu Asn Glu Leu Leu Ser Tyr Thr Asp Leu
        115                 120                 125

Ile Leu Leu Asp Leu Lys His Ile Asp Glu Lys Lys His Arg Lys Leu
```

```
            130                 135                 140
Thr Gly Lys Thr Asn Lys His Ile Leu Gln Phe Ala Gln Phe Leu Ser
145                 150                 155                 160

Glu Lys Asn Val Pro Val Trp Ile Arg His Val Leu Val Pro Thr Ile
                165                 170                 175

Thr Asp Asp Pro Asn Asp Leu Arg Arg Leu Ala Ala Phe Ile Arg Thr
            180                 185                 190

Leu Lys Asn Val Lys Lys Ile Glu Ile Leu Pro Tyr His Lys Leu Gly
                195                 200                 205

Val Tyr Lys Trp Lys Ala Leu Gly Leu Lys Tyr Pro Leu Glu Gly Ile
        210                 215                 220

Glu Pro Pro Ser Glu Glu Ser Val Gln Met Ala Gln Arg Ile Leu Asn
225                 230                 235                 240

Gly Thr Glu Asp Thr Val Ser Leu Ala
                245

<210> SEQ ID NO 41
<211> LENGTH: 2250
<212> TYPE: DNA
<213> ORGANISM: Geobacillus thermoglucosidans
<220> FEATURE:
<221> NAME/KEY: CDS
<222> LOCATION: (1)..(2250)

<400> SEQUENCE: 41 atg aaa caa gcc act gtt gta ttg gac cct tgg cgc aat ttt aaa ggg    48
Met Lys Gln Ala Thr Val Val Leu Asp Pro Trp Arg Asn Phe Lys Gly
1               5                   10                  15 tca aaa tgg aaa aaa tcg att gac gtc cgt gat ttt att tta aac aat    96
Ser Lys Trp Lys Lys Ser Ile Asp Val Arg Asp Phe Ile Leu Asn Asn
            20                  25                  30 gta acc gtt tac tac ggg gat gaa tca ttc cta gaa ggg cct aca gaa   144
Val Thr Val Tyr Tyr Gly Asp Glu Ser Phe Leu Glu Gly Pro Thr Glu
        35                  40                  45 gca acg aaa aaa cta tgg gaa caa gtg atg gaa ttg tcg aaa caa gaa   192
Ala Thr Lys Lys Leu Trp Glu Gln Val Met Glu Leu Ser Lys Gln Glu
    50                  55                  60 cgc gaa aaa ggc ggc gtc ctt gat atg gac aca tcg att gtt tcg acc   240
Arg Glu Lys Gly Gly Val Leu Asp Met Asp Thr Ser Ile Val Ser Thr
65                  70                  75                  80 atc act tcc cac gga cca ggt tat tta aac aaa gac ttg gaa aaa atc   288
Ile Thr Ser His Gly Pro Gly Tyr Leu Asn Lys Asp Leu Glu Lys Ile
                85                  90                  95 gta ggt ttt caa aca gat aaa ccg ttt aag cgt gca tta atg ccg ttt   336
Val Gly Phe Gln Thr Asp Lys Pro Phe Lys Arg Ala Leu Met Pro Phe
            100                 105                 110 ggc ggc att cgc atg gcg caa caa tca tgc gaa gca tac ggt tac aaa   384
Gly Gly Ile Arg Met Ala Gln Gln Ser Cys Glu Ala Tyr Gly Tyr Lys
        115                 120                 125 gta agc gac gaa gtg aaa aaa atc ttt acg gaa tac cgg aaa aca cac   432
Val Ser Asp Glu Val Lys Lys Ile Phe Thr Glu Tyr Arg Lys Thr His
    130                 135                 140 aac caa ggt gtg ttt gac gtt tac acc gac gag atg aga tta gcg cgc   480
Asn Gln Gly Val Phe Asp Val Tyr Thr Asp Glu Met Arg Leu Ala Arg
145                 150                 155                 160 aaa gca gga atc atc acc ggc ctt cct gat gcg tac gga cgc ggc cgt   528
Lys Ala Gly Ile Ile Thr Gly Leu Pro Asp Ala Tyr Gly Arg Gly Arg
                165                 170                 175 atc atc ggc gac tat cgt cgc gtc gcg tta tac ggt gtc gat cgt ttg   576
```

```
Ile Ile Gly Asp Tyr Arg Arg Val Ala Leu Tyr Gly Val Asp Arg Leu
            180                 185                 190 atc gaa gaa aaa caa aaa gat ttg aaa aac act ggc gca aga acg atg    624
Ile Glu Glu Lys Gln Lys Asp Leu Lys Asn Thr Gly Ala Arg Thr Met
        195                 200                 205 acc gaa gac att atc cgt ctt cgc gaa gaa att tca gag caa att cgc    672
Thr Glu Asp Ile Ile Arg Leu Arg Glu Glu Ile Ser Glu Gln Ile Arg
    210                 215                 220 gca tta aac gag tta aaa caa atg gcg tta agc tat gga tat gat att    720
Ala Leu Asn Glu Leu Lys Gln Met Ala Leu Ser Tyr Gly Tyr Asp Ile
225                 230                 235                 240 tcc aaa ccg gca cgg aac gca cat gaa gca ttc caa tgg ctc tat ttc    768
Ser Lys Pro Ala Arg Asn Ala His Glu Ala Phe Gln Trp Leu Tyr Phe
                245                 250                 255 gct tat ctt gct gct att aaa gaa caa aac ggc gcg gcg atg agc tta    816
Ala Tyr Leu Ala Ala Ile Lys Glu Gln Asn Gly Ala Ala Met Ser Leu
            260                 265                 270 ggg cgc gtt tcc acc ttc ttg gat att tat atc gag cgc gac ttt gca    864
Gly Arg Val Ser Thr Phe Leu Asp Ile Tyr Ile Glu Arg Asp Phe Ala
        275                 280                 285 gaa ggc aca tta acg gaa aaa gaa gcg caa gaa ctt gtc gac cat ttt    912
Glu Gly Thr Leu Thr Glu Lys Glu Ala Gln Glu Leu Val Asp His Phe
    290                 295                 300 gtg atg aaa ttg cgc ctt gtc aaa ttt gcc aga acg ccg gaa tat aac    960
Val Met Lys Leu Arg Leu Val Lys Phe Ala Arg Thr Pro Glu Tyr Asn
305                 310                 315                 320 gaa ctg ttt agc gga gac ccg aca tgg gtt acc gaa tcg atc ggc gga    1008
Glu Leu Phe Ser Gly Asp Pro Thr Trp Val Thr Glu Ser Ile Gly Gly
                325                 330                 335 att gcc att gat ggc cgt ccg tta gtg aca aag aac tcg ttc cgt ttc    1056
Ile Ala Ile Asp Gly Arg Pro Leu Val Thr Lys Asn Ser Phe Arg Phe
            340                 345                 350 ctt cat acg tta gat aac tta gga cct gcg cca gag cca aac tta aca    1104
Leu His Thr Leu Asp Asn Leu Gly Pro Ala Pro Glu Pro Asn Leu Thr
        355                 360                 365 gta ctt tgg tcg aaa caa ttg ccg gaa gca ttc aaa gag tat tgc gcg    1152
Val Leu Trp Ser Lys Gln Leu Pro Glu Ala Phe Lys Glu Tyr Cys Ala
    370                 375                 380 aaa atg tcg atc aaa aca agc tcg att caa tat gaa aat gac gac tta    1200
Lys Met Ser Ile Lys Thr Ser Ser Ile Gln Tyr Glu Asn Asp Asp Leu
385                 390                 395                 400 atg cgc gtc gaa ttt ggc gat gat tac gga att gct tgc tgc gta tca    1248
Met Arg Val Glu Phe Gly Asp Asp Tyr Gly Ile Ala Cys Cys Val Ser
                405                 410                 415 gcg atg cga atc ggc aaa caa atg caa ttt ttc gga gcg cgc gcc aac    1296
Ala Met Arg Ile Gly Lys Gln Met Gln Phe Phe Gly Ala Arg Ala Asn
            420                 425                 430 ctc gcc aaa gca ttg tta tat gcg att aac ggc ggt gtc gat gaa aaa    1344
Leu Ala Lys Ala Leu Leu Tyr Ala Ile Asn Gly Gly Val Asp Glu Lys
        435                 440                 445 ttg aaa atc caa gtt ggc cct gaa ttt gcg ccg att acc tcc gaa tat    1392
Leu Lys Ile Gln Val Gly Pro Glu Phe Ala Pro Ile Thr Ser Glu Tyr
    450                 455                 460 tta aat tat gat gaa gtg atg cat aaa ttc gat caa gtg ctt gaa tgg    1440
Leu Asn Tyr Asp Glu Val Met His Lys Phe Asp Gln Val Leu Glu Trp
465                 470                 475                 480 ctt gcc gaa ctt tat att aac aca ctg aat gtc atc cat tac atg cac    1488
Leu Ala Glu Leu Tyr Ile Asn Thr Leu Asn Val Ile His Tyr Met His
                485                 490                 495
```

```
gac aaa tat tgt tat gaa cgc att gaa atg gcg ctt cac gat act cac    1536
Asp Lys Tyr Cys Tyr Glu Arg Ile Glu Met Ala Leu His Asp Thr His
        500                 505                 510 gtt tta cgc aca atg gcc act ggc att gcc gga ttg tca gtt gtc gtc    1584
Val Leu Arg Thr Met Ala Thr Gly Ile Ala Gly Leu Ser Val Val Val
        515                 520                 525 gat tcg tta agc gcg atc aaa tat gca aaa gtc aaa ccg atc cgc gat    1632
Asp Ser Leu Ser Ala Ile Lys Tyr Ala Lys Val Lys Pro Ile Arg Asp
530                 535                 540 gaa aac ggc att gct gtt gat ttt gaa atg gaa ggc gac ttc ccg aaa    1680
Glu Asn Gly Ile Ala Val Asp Phe Glu Met Glu Gly Asp Phe Pro Lys
545                 550                 555                 560 tac gga aat aac gat gat cgc gtc gac caa att gcc gtt gat tta gtc    1728
Tyr Gly Asn Asn Asp Asp Arg Val Asp Gln Ile Ala Val Asp Leu Val
            565                 570                 575 gaa cgt ttt atg acg aaa ttg aaa aaa cat aaa aca tat cgc gat tcg    1776
Glu Arg Phe Met Thr Lys Leu Lys Lys His Lys Thr Tyr Arg Asp Ser
            580                 585                 590 aaa cat acg cta tct att tta aca att acg tct aac gtt gta tac ggg    1824
Lys His Thr Leu Ser Ile Leu Thr Ile Thr Ser Asn Val Val Tyr Gly
                595                 600                 605 aaa aag acc gga aat aca cca gat ggc cgc cgc gct ggc gaa ccg ttt    1872
Lys Lys Thr Gly Asn Thr Pro Asp Gly Arg Arg Ala Gly Glu Pro Phe
610                 615                 620 gcc cca gga gca aac ccg ttg cac ggc gtt gac acg aaa gga gcg ctc    1920
Ala Pro Gly Ala Asn Pro Leu His Gly Val Asp Thr Lys Gly Ala Leu
625                 630                 635                 640 gct tcg cta agc tct gtc gcg aaa tta cca tat gaa cat gca tta gat    1968
Ala Ser Leu Ser Ser Val Ala Lys Leu Pro Tyr Glu His Ala Leu Asp
            645                 650                 655 ggc att tcg aat acg ttc tcg atc gtg ccg aaa gcg tta gga aaa gag    2016
Gly Ile Ser Asn Thr Phe Ser Ile Val Pro Lys Ala Leu Gly Lys Glu
            660                 665                 670 gaa gga gac cgt gtc cgc aac ctt gtc gcc gtt tta gac gga tac atg    2064
Glu Gly Asp Arg Val Arg Asn Leu Val Ala Val Leu Asp Gly Tyr Met
                675                 680                 685 gaa aaa ggc ggg cat cat ctc aac att aac gtg ttg aac cgc gaa aca    2112
Glu Lys Gly Gly His His Leu Asn Ile Asn Val Leu Asn Arg Glu Thr
690                 695                 700 ttg tta gat gcg atg gaa cat cca gaa aaa tat ccg caa tta acg att    2160
Leu Leu Asp Ala Met Glu His Pro Glu Lys Tyr Pro Gln Leu Thr Ile
705                 710                 715                 720 cgc gtt tct gga tat gcc gtc aac ttc ata aaa tta acg cgc gaa caa    2208
Arg Val Ser Gly Tyr Ala Val Asn Phe Ile Lys Leu Thr Arg Glu Gln
            725                 730                 735 caa atc gat gtc att aac cgc acg ttc cac gaa acg atg taa            2250
Gln Ile Asp Val Ile Asn Arg Thr Phe His Glu Thr Met
            740                 745

<210> SEQ ID NO 42
<211> LENGTH: 749
<212> TYPE: PRT
<213> ORGANISM: Geobacillus thermoglucosidans

<400> SEQUENCE: 42

Met Lys Gln Ala Thr Val Val Leu Asp Pro Trp Arg Asn Phe Lys Gly
1               5                   10                  15

Ser Lys Trp Lys Lys Ser Ile Asp Val Arg Asp Phe Ile Leu Asn Asn
            20                  25                  30

Val Thr Val Tyr Tyr Gly Asp Glu Ser Phe Leu Glu Gly Pro Thr Glu
```

```
                35                  40                  45
Ala Thr Lys Lys Leu Trp Glu Gln Val Met Glu Leu Ser Lys Gln Glu
 50                  55                  60

Arg Glu Lys Gly Gly Val Leu Asp Met Asp Thr Ser Ile Val Ser Thr
 65                  70                  75                  80

Ile Thr Ser His Gly Pro Gly Tyr Leu Asn Lys Asp Leu Glu Lys Ile
                 85                  90                  95

Val Gly Phe Gln Thr Asp Lys Pro Phe Lys Arg Ala Leu Met Pro Phe
                100                 105                 110

Gly Gly Ile Arg Met Ala Gln Gln Ser Cys Glu Ala Tyr Gly Tyr Lys
                115                 120                 125

Val Ser Asp Glu Val Lys Lys Ile Phe Thr Glu Tyr Arg Lys Thr His
130                 135                 140

Asn Gln Gly Val Phe Asp Val Tyr Thr Asp Glu Met Arg Leu Ala Arg
145                 150                 155                 160

Lys Ala Gly Ile Ile Thr Gly Leu Pro Asp Ala Tyr Gly Arg Gly Arg
                165                 170                 175

Ile Ile Gly Asp Tyr Arg Arg Val Ala Leu Tyr Gly Val Asp Arg Leu
                180                 185                 190

Ile Glu Glu Lys Gln Lys Asp Leu Lys Asn Thr Gly Ala Arg Thr Met
                195                 200                 205

Thr Glu Asp Ile Ile Arg Leu Arg Glu Glu Ile Ser Glu Gln Ile Arg
210                 215                 220

Ala Leu Asn Glu Leu Lys Gln Met Ala Leu Ser Tyr Gly Tyr Asp Ile
225                 230                 235                 240

Ser Lys Pro Ala Arg Asn Ala His Glu Ala Phe Gln Trp Leu Tyr Phe
                245                 250                 255

Ala Tyr Leu Ala Ala Ile Lys Glu Gln Asn Gly Ala Ala Met Ser Leu
                260                 265                 270

Gly Arg Val Ser Thr Phe Leu Asp Ile Tyr Ile Glu Arg Asp Phe Ala
                275                 280                 285

Glu Gly Thr Leu Thr Glu Lys Glu Ala Gln Glu Leu Val Asp His Phe
290                 295                 300

Val Met Lys Leu Arg Leu Val Lys Phe Ala Arg Thr Pro Glu Tyr Asn
305                 310                 315                 320

Glu Leu Phe Ser Gly Asp Pro Thr Trp Val Thr Glu Ser Ile Gly Gly
                325                 330                 335

Ile Ala Ile Asp Gly Arg Pro Leu Val Thr Lys Asn Ser Phe Arg Phe
                340                 345                 350

Leu His Thr Leu Asp Asn Leu Gly Pro Ala Pro Glu Pro Asn Leu Thr
                355                 360                 365

Val Leu Trp Ser Lys Gln Leu Pro Glu Ala Phe Lys Glu Tyr Cys Ala
                370                 375                 380

Lys Met Ser Ile Lys Thr Ser Ser Ile Gln Tyr Glu Asn Asp Asp Leu
385                 390                 395                 400

Met Arg Val Glu Phe Gly Asp Asp Tyr Gly Ile Ala Cys Cys Val Ser
                405                 410                 415

Ala Met Arg Ile Gly Lys Gln Met Gln Phe Phe Gly Ala Arg Ala Asn
                420                 425                 430

Leu Ala Lys Ala Leu Leu Tyr Ala Ile Asn Gly Gly Val Asp Glu Lys
                435                 440                 445

Leu Lys Ile Gln Val Gly Pro Glu Phe Ala Pro Ile Thr Ser Glu Tyr
                450                 455                 460
```

Leu Asn Tyr Asp Glu Val Met His Lys Phe Asp Gln Val Leu Glu Trp
465                 470                 475                 480

Leu Ala Glu Leu Tyr Ile Asn Thr Leu Asn Val Ile His Tyr Met His
                485                 490                 495

Asp Lys Tyr Cys Tyr Glu Arg Ile Glu Met Ala Leu His Asp Thr His
            500                 505                 510

Val Leu Arg Thr Met Ala Thr Gly Ile Ala Gly Leu Ser Val Val Val
        515                 520                 525

Asp Ser Leu Ser Ala Ile Lys Tyr Ala Lys Val Lys Pro Ile Arg Asp
530                 535                 540

Glu Asn Gly Ile Ala Val Asp Phe Glu Met Gly Gly Asp Phe Pro Lys
545                 550                 555                 560

Tyr Gly Asn Asn Asp Asp Arg Val Asp Gln Ile Ala Val Asp Leu Val
                565                 570                 575

Glu Arg Phe Met Thr Lys Leu Lys Lys His Lys Thr Tyr Arg Asp Ser
            580                 585                 590

Lys His Thr Leu Ser Ile Leu Thr Ile Thr Ser Asn Val Val Tyr Gly
        595                 600                 605

Lys Lys Thr Gly Asn Thr Pro Asp Gly Arg Arg Ala Gly Glu Pro Phe
610                 615                 620

Ala Pro Gly Ala Asn Pro Leu His Gly Arg Asp Thr Lys Gly Ala Leu
625                 630                 635                 640

Ala Ser Leu Ser Ser Val Ala Lys Leu Pro Tyr Glu His Ala Leu Asp
                645                 650                 655

Gly Ile Ser Asn Thr Phe Ser Ile Val Pro Lys Ala Leu Gly Lys Glu
            660                 665                 670

Glu Gly Asp Arg Val Arg Asn Leu Val Ala Val Leu Asp Gly Tyr Met
        675                 680                 685

Glu Lys Gly Gly His His Leu Asn Ile Asn Val Leu Asn Arg Glu Thr
690                 695                 700

Leu Leu Asp Ala Met Glu His Pro Glu Lys Tyr Pro Gln Leu Thr Ile
705                 710                 715                 720

Arg Val Ser Gly Tyr Ala Val Asn Phe Ile Lys Leu Thr Arg Glu Gln
                725                 730                 735

Gln Ile Asp Val Ile Asn Arg Thr Phe His Glu Thr Met
            740                 745

```
<210> SEQ ID NO 43
<211> LENGTH: 2604
<212> TYPE: DNA
<213> ORGANISM: Geobacillus thermoglucosidans
<220> FEATURE:
<221> NAME/KEY: CDS
<222> LOCATION: (1)..(2604)

<400> SEQUENCE: 43
```

| | | | | | | | | | | | | | | | | |
|---|---|---|---|---|---|---|---|---|---|---|---|---|---|---|---|---|
| atg | gct | gtg | gag | gag | aga | gtc | gtc | gat | aaa | aaa | atc | gaa | gta | gca | aaa | 48 |
| Met | Ala | Val | Glu | Glu | Arg | Val | Val | Asp | Lys | Lys | Ile | Glu | Val | Ala | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| atg | att | gat | gag | ctt | gtc | gct | aat | gca | cag | aaa | gcg | ttg | gaa | caa | att | 96 |
| Met | Ile | Asp | Glu | Leu | Val | Ala | Asn | Ala | Gln | Lys | Ala | Leu | Glu | Gln | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| cgc | gct | tac | gat | caa | gaa | acg | atc | gat | cat | atc | gtg | aaa | gaa | atg | gcg | 144 |
| Arg | Ala | Tyr | Asp | Gln | Glu | Thr | Ile | Asp | His | Ile | Val | Lys | Glu | Met | Ala | |
| | | 35 | | | | | 40 | | | | | 45 | | | | |

| | | | | | | | | | | | | | | | | |
|---|---|---|---|---|---|---|---|---|---|---|---|---|---|---|---|---|
| tta | gcc | ggg | ctc | gac | aag | cat | atg | gca | tta | gcc | aag | ctt | gca | gta | gaa | 192 |

```
                Leu Ala Gly Leu Asp Lys His Met Ala Leu Ala Lys Leu Ala Val Glu
                    50                  55                  60 gaa aca aaa cgc ggt gta tat gaa gat aaa atc ata aaa aac ctt ttt              240
Glu Thr Lys Arg Gly Val Tyr Glu Asp Lys Ile Ile Lys Asn Leu Phe
 65                  70                  75                  80 gcg aca gaa tat ata tac cac aat att aag tat gat aaa aca gtc ggg              288
Ala Thr Glu Tyr Ile Tyr His Asn Ile Lys Tyr Asp Lys Thr Val Gly
                 85                  90                  95 att att cat gaa aat ccg cat gaa gaa att atc gaa att gct gag cct              336
Ile Ile His Glu Asn Pro His Glu Glu Ile Ile Glu Ile Ala Glu Pro
            100                 105                 110 gtt ggt gtt att gct ggg att acg cca gtg aca aac ccg aca tcg aca              384
Val Gly Val Ile Ala Gly Ile Thr Pro Val Thr Asn Pro Thr Ser Thr
            115                 120                 125 acg atg ttt aaa gcg tta atc tcg ata aaa aca cgc aac ccg att att              432
Thr Met Phe Lys Ala Leu Ile Ser Ile Lys Thr Arg Asn Pro Ile Ile
        130                 135                 140 ttc gct ttc cat cca tcg gcg caa cga tgc agc agc gaa gcg gca aga              480
Phe Ala Phe His Pro Ser Ala Gln Arg Cys Ser Ser Glu Ala Ala Arg
145                 150                 155                 160 gtg ctg cgc gat gcg gcg gtc cgg gca ggg gct cca gaa cat tgc att              528
Val Leu Arg Asp Ala Ala Val Arg Ala Gly Ala Pro Glu His Cys Ile
                165                 170                 175 caa tgg att gaa act cct tcg ctt gat gca acc aat cag ctt atg cac              576
Gln Trp Ile Glu Thr Pro Ser Leu Asp Ala Thr Asn Gln Leu Met His
            180                 185                 190 cat cct ggc gtt tct ctc att ttg gca act ggt ggc gcc ggc atg gtg              624
His Pro Gly Val Ser Leu Ile Leu Ala Thr Gly Gly Ala Gly Met Val
            195                 200                 205 aaa gca gcg tac agc tct gga aaa cca gct ttg ggc gtc gga cct ggc              672
Lys Ala Ala Tyr Ser Ser Gly Lys Pro Ala Leu Gly Val Gly Pro Gly
        210                 215                 220 aat gtg cct tgc tat att gaa aaa acg gca aac ata aaa cgg gcg gta              720
Asn Val Pro Cys Tyr Ile Glu Lys Thr Ala Asn Ile Lys Arg Ala Val
225                 230                 235                 240 aat gac tta att tta tcg aaa acg ttt gat aac ggc atg att tgc gct              768
Asn Asp Leu Ile Leu Ser Lys Thr Phe Asp Asn Gly Met Ile Cys Ala
                245                 250                 255 tct gaa caa gca gtc att att gat aaa gaa att tat gaa caa gta aag              816
Ser Glu Gln Ala Val Ile Ile Asp Lys Glu Ile Tyr Glu Gln Val Lys
            260                 265                 270 aaa gaa atg ata gaa aac cat tgt tat ttc tta aat gaa gaa gaa aag              864
Lys Glu Met Ile Glu Asn His Cys Tyr Phe Leu Asn Glu Glu Glu Lys
            275                 280                 285 aaa aaa gta gaa aaa ctc gtt atc aat gaa aat aca tgc gcc gtc aac              912
Lys Lys Val Glu Lys Leu Val Ile Asn Glu Asn Thr Cys Ala Val Asn
        290                 295                 300 ccg gat atc gtc gga aag cca gct tat gaa att gcg aaa atg gcc ggc              960
Pro Asp Ile Val Gly Lys Pro Ala Tyr Glu Ile Ala Lys Met Ala Gly
305                 310                 315                 320 atc gct gtg ccg gaa gac aca aaa att ctt gtt gct gag tta aaa ggg             1008
Ile Ala Val Pro Glu Asp Thr Lys Ile Leu Val Ala Glu Leu Lys Gly
                325                 330                 335 gtc ggg cca aaa tat ccg ttg tct cgg gaa aaa tta agc cct gtc ctt             1056
Val Gly Pro Lys Tyr Pro Leu Ser Arg Glu Lys Leu Ser Pro Val Leu
            340                 345                 350 gct tgc tat aaa gtt aac agc acg gaa gaa gga ttt aag cgc tgt gaa             1104
Ala Cys Tyr Lys Val Asn Ser Thr Glu Glu Gly Phe Lys Arg Cys Glu
        355                 360                 365
```

| | | |
|---|---|---|
| gaa atg ctg gaa ttt ggc ggc ttg gga cat tcg gct gtc atc cat tcc<br>Glu Met Leu Glu Phe Gly Gly Leu Gly His Ser Ala Val Ile His Ser<br>370                        375                    380 | 1152 |
| gat aat caa aac gtg gtt acc gaa ttt ggc aaa cgg atg aaa gcg gga<br>Asp Asn Gln Asn Val Val Thr Glu Phe Gly Lys Arg Met Lys Ala Gly<br>385                        390                   395                   400 | 1200 |
| cgg att atc gtt aat gcg cca tct tcg caa gga gca atc ggc gat att<br>Arg Ile Ile Val Asn Ala Pro Ser Ser Gln Gly Ala Ile Gly Asp Ile<br>                          405                   410                   415 | 1248 |
| tac aat gcg tac att ccg tca tta acg ctg gga tgc ggc aca ttt ggc<br>Tyr Asn Ala Tyr Ile Pro Ser Leu Thr Leu Gly Cys Gly Thr Phe Gly<br>                   420                   425                   430 | 1296 |
| gga aac tct gtt tcg aca aac gtc agt gcg att cat ctt atc aat ata<br>Gly Asn Ser Val Ser Thr Asn Val Ser Ala Ile His Leu Ile Asn Ile<br>435                        440                    445 | 1344 |
| aaa aga atg gca aaa agg acg gta aat atg caa tgg ttt aaa gtg ccg<br>Lys Arg Met Ala Lys Arg Thr Val Asn Met Gln Trp Phe Lys Val Pro<br>450                        455                   460 | 1392 |
| ccg aaa att tat ttc gaa aaa aat gct gta caa tac tta gcg aaa atg<br>Pro Lys Ile Tyr Phe Glu Lys Asn Ala Val Gln Tyr Leu Ala Lys Met<br>465                        470                    475                   480 | 1440 |
| ccg gat att tcc aga gct ttt atc gtc acc gac ccg gga atg gtc aag<br>Pro Asp Ile Ser Arg Ala Phe Ile Val Thr Asp Pro Gly Met Val Lys<br>                   485                   490                   495 | 1488 |
| ctc gga tat gtc gat aaa gtg ctg tat tac ttg cgc aga cgc ccg gat<br>Leu Gly Tyr Val Asp Lys Val Leu Tyr Tyr Leu Arg Arg Arg Pro Asp<br>                   500                   505                   510 | 1536 |
| tat gtg cat agt gaa att ttc tcc gaa gta gag cca gat cct tca att<br>Tyr Val His Ser Glu Ile Phe Ser Glu Val Glu Pro Asp Pro Ser Ile<br>                   515                   520                   525 | 1584 |
| gag acg gta atg aaa ggt gtc gat atg atg aga agt ttc gag ccg gat<br>Glu Thr Val Met Lys Gly Val Asp Met Met Arg Ser Phe Glu Pro Asp<br>      530                       535                   540 | 1632 |
| gtg att atc gcg ctt gga ggc ggc tcg cca atg gat gcg gca aaa gcg<br>Val Ile Ile Ala Leu Gly Gly Gly Ser Pro Met Asp Ala Ala Lys Ala<br>545                        550                    555                   560 | 1680 |
| atg tgg ctc ttt tac gag cat ccg aca gcg gat ttc aac gca tta aaa<br>Met Trp Leu Phe Tyr Glu His Pro Thr Ala Asp Phe Asn Ala Leu Lys<br>                   565                   570                   575 | 1728 |
| caa aaa ttt tta gat att cga aaa cgc gtt tat aaa tat cca aaa ctg<br>Gln Lys Phe Leu Asp Ile Arg Lys Arg Val Tyr Lys Tyr Pro Lys Leu<br>                580                   585                   590 | 1776 |
| ggc caa aaa gcg aaa ttt gtc gcc att ccg acg aca tca gga aca gga<br>Gly Gln Lys Ala Lys Phe Val Ala Ile Pro Thr Thr Ser Gly Thr Gly<br>               595                   600                   605 | 1824 |
| tcg gaa gta acg tcc ttt gcc gtc att acc gat aaa aaa acg aat ata<br>Ser Glu Val Thr Ser Phe Ala Val Ile Thr Asp Lys Lys Thr Asn Ile<br>      610                       615                   620 | 1872 |
| aaa tat ccg ttg gca gat tat gaa ttg aca ccg gac gtc gcg att gtg<br>Lys Tyr Pro Leu Ala Asp Tyr Glu Leu Thr Pro Asp Val Ala Ile Val<br>625                        630                    635                   640 | 1920 |
| gat ccg caa ttt gtc atg acc gtg cca aaa cat gtc acc gcc gat acg<br>Asp Pro Gln Phe Val Met Thr Val Pro Lys His Val Thr Ala Asp Thr<br>                   645                   650                   655 | 1968 |
| gga atg gat gta ttg aca cat gcg atc gaa gcg tat gtc tcc aat atg<br>Gly Met Asp Val Leu Thr His Ala Ile Glu Ala Tyr Val Ser Asn Met<br>                660                   665                   670 | 2016 |
| gca aat gat tat acc gat ggt ctt gcc atg aaa gca atc caa ctc gta<br>Ala Asn Asp Tyr Thr Asp Gly Leu Ala Met Lys Ala Ile Gln Leu Val<br>675                        680                    685 | 2064 |

-continued

```
ttt gaa tat ttg ccg cgg gca tat caa aac gga gcg gat gag ctt gcc      2112
Phe Glu Tyr Leu Pro Arg Ala Tyr Gln Asn Gly Ala Asp Glu Leu Ala
    690             695                 700 cgg gag aaa atg cat aac gcc tct acg att gcg gga atg gca ttt gcc      2160
Arg Glu Lys Met His Asn Ala Ser Thr Ile Ala Gly Met Ala Phe Ala
705                 710                 715                 720 aac gcg ttt tta ggc att aac cat agt ttg gct cat aaa ctt ggc gcg      2208
Asn Ala Phe Leu Gly Ile Asn His Ser Leu Ala His Lys Leu Gly Ala
                725                 730                 735 gaa ttc cat att ccg cat ggg cgc gcg aat acc att ttg atg ccg cat      2256
Glu Phe His Ile Pro His Gly Arg Ala Asn Thr Ile Leu Met Pro His
            740                 745                 750 gtc att cgc tat aac gca gcg aaa ccg aaa aaa ttt acc gca ttt ccg      2304
Val Ile Arg Tyr Asn Ala Ala Lys Pro Lys Lys Phe Thr Ala Phe Pro
        755                 760                 765 aaa tac gaa tat ttc aaa gcg gac cag cgc tat gca gaa att gcg aga      2352
Lys Tyr Glu Tyr Phe Lys Ala Asp Gln Arg Tyr Ala Glu Ile Ala Arg
    770                 775                 780 atg ctc ggc ttg ccg gcc cgc aca acg gaa gaa ggg gtc gaa agc ctc      2400
Met Leu Gly Leu Pro Ala Arg Thr Thr Glu Glu Gly Val Glu Ser Leu
785                 790                 795                 800 gtt cag gcg atc att aag ctg gca aaa cag ttg gat atg ccg ctg agc      2448
Val Gln Ala Ile Ile Lys Leu Ala Lys Gln Leu Asp Met Pro Leu Ser
                805                 810                 815 att gaa gca tgc ggc gtc agc aaa caa gaa ttt gaa agc aaa gtt gaa      2496
Ile Glu Ala Cys Gly Val Ser Lys Gln Glu Phe Glu Ser Lys Val Glu
            820                 825                 830 aaa tta gcc gaa ttg gct ttc gaa gac caa tgt act act gct aac ccg      2544
Lys Leu Ala Glu Leu Ala Phe Glu Asp Gln Cys Thr Thr Ala Asn Pro
        835                 840                 845 aaa ctc ccg ctt gtt agc gat tta gtt cat att tat cgc caa gcg ttt      2592
Lys Leu Pro Leu Val Ser Asp Leu Val His Ile Tyr Arg Gln Ala Phe
    850                 855                 860 aaa gga gtt taa                                                      2604
Lys Gly Val
865
```

<210> SEQ ID NO 44
<211> LENGTH: 867
<212> TYPE: PRT
<213> ORGANISM: Geobacillus thermoglucosidans

<400> SEQUENCE: 44

```
Met Ala Val Glu Glu Arg Val Val Asp Lys Lys Ile Glu Val Ala Lys
1               5                   10                  15

Met Ile Asp Glu Leu Val Ala Asn Ala Gln Lys Ala Leu Glu Gln Ile
            20                  25                  30

Arg Ala Tyr Asp Gln Glu Thr Ile Asp His Ile Val Lys Glu Met Ala
        35                  40                  45

Leu Ala Gly Leu Asp Lys His Met Ala Leu Ala Lys Leu Ala Val Glu
    50                  55                  60

Glu Thr Lys Arg Gly Val Tyr Glu Asp Lys Ile Ile Lys Asn Leu Phe
65                  70                  75                  80

Ala Thr Glu Tyr Ile Tyr His Asn Ile Lys Tyr Asp Lys Thr Val Gly
                85                  90                  95

Ile Ile His Glu Asn Pro His Glu Glu Ile Glu Ile Ala Glu Pro
            100                 105                 110

Val Gly Val Ile Ala Gly Ile Thr Pro Val Thr Asn Pro Thr Ser Thr
```

```
            115                 120                 125
Thr Met Phe Lys Ala Leu Ile Ser Ile Lys Thr Arg Asn Pro Ile Ile
    130                 135                 140

Phe Ala Phe His Pro Ser Ala Gln Arg Cys Ser Ser Glu Ala Ala Arg
145                 150                 155                 160

Val Leu Arg Asp Ala Val Arg Ala Gly Ala Pro Glu His Cys Ile
                165                 170                 175

Gln Trp Ile Glu Thr Pro Ser Leu Asp Ala Thr Asn Gln Leu Met His
            180                 185                 190

His Pro Gly Val Ser Leu Ile Leu Ala Thr Gly Gly Ala Gly Met Val
        195                 200                 205

Lys Ala Ala Tyr Ser Ser Gly Lys Pro Ala Leu Gly Val Gly Pro Gly
    210                 215                 220

Asn Val Pro Cys Tyr Ile Glu Lys Thr Ala Asn Ile Lys Arg Ala Val
225                 230                 235                 240

Asn Asp Leu Ile Leu Ser Lys Thr Phe Asp Asn Gly Met Ile Cys Ala
                245                 250                 255

Ser Glu Gln Ala Val Ile Ile Asp Lys Glu Ile Tyr Glu Gln Val Lys
            260                 265                 270

Lys Glu Met Ile Glu Asn His Cys Tyr Phe Leu Asn Glu Glu Lys
        275                 280                 285

Lys Lys Val Glu Lys Leu Val Ile Asn Glu Asn Thr Cys Ala Val Asn
    290                 295                 300

Pro Asp Ile Val Gly Lys Pro Ala Tyr Glu Ile Ala Lys Met Ala Gly
305                 310                 315                 320

Ile Ala Val Pro Glu Asp Thr Lys Ile Leu Val Ala Glu Leu Lys Gly
                325                 330                 335

Val Gly Pro Lys Tyr Pro Leu Ser Arg Glu Lys Leu Ser Pro Val Leu
            340                 345                 350

Ala Cys Tyr Lys Val Asn Ser Thr Glu Glu Gly Phe Lys Arg Cys Glu
        355                 360                 365

Glu Met Leu Glu Phe Gly Gly Leu Gly His Ser Ala Val Ile His Ser
    370                 375                 380

Asp Asn Gln Asn Val Val Thr Glu Phe Gly Lys Arg Met Lys Ala Gly
385                 390                 395                 400

Arg Ile Ile Val Asn Ala Pro Ser Ser Gln Gly Ala Ile Gly Asp Ile
                405                 410                 415

Tyr Asn Ala Tyr Ile Pro Ser Leu Thr Leu Gly Cys Gly Thr Phe Gly
            420                 425                 430

Gly Asn Ser Val Ser Thr Asn Val Ser Ala Ile His Leu Ile Asn Ile
        435                 440                 445

Lys Arg Met Ala Lys Arg Thr Val Asn Met Gln Trp Phe Lys Val Pro
    450                 455                 460

Pro Lys Ile Tyr Phe Glu Lys Asn Ala Val Gln Tyr Leu Ala Lys Met
465                 470                 475                 480

Pro Asp Ile Ser Arg Ala Phe Ile Val Thr Asp Pro Gly Met Val Lys
                485                 490                 495

Leu Gly Tyr Val Asp Lys Val Leu Tyr Tyr Leu Arg Arg Arg Pro Asp
            500                 505                 510

Tyr Val His Ser Glu Ile Phe Ser Glu Val Glu Pro Asp Pro Ser Ile
        515                 520                 525

Glu Thr Val Met Lys Gly Val Asp Met Met Arg Ser Phe Glu Pro Asp
    530                 535                 540
```

```
Val Ile Ile Ala Leu Gly Gly Ser Pro Met Asp Ala Ala Lys Ala
545                 550                 555                 560

Met Trp Leu Phe Tyr Glu His Pro Thr Ala Asp Phe Asn Ala Leu Lys
                565                 570                 575

Gln Lys Phe Leu Asp Ile Arg Lys Arg Val Tyr Lys Tyr Pro Lys Leu
            580                 585                 590

Gly Gln Lys Ala Lys Phe Val Ala Ile Pro Thr Thr Ser Gly Thr Gly
            595                 600                 605

Ser Glu Val Thr Ser Phe Ala Val Ile Thr Asp Lys Lys Thr Asn Ile
    610                 615                 620

Lys Tyr Pro Leu Ala Asp Tyr Glu Leu Thr Pro Asp Val Ala Ile Val
625                 630                 635                 640

Asp Pro Gln Phe Val Met Thr Val Pro Lys His Val Thr Ala Asp Thr
                645                 650                 655

Gly Met Asp Val Leu Thr His Ala Ile Glu Ala Tyr Val Ser Asn Met
            660                 665                 670

Ala Asn Asp Tyr Thr Asp Gly Leu Ala Met Lys Ala Ile Gln Leu Val
            675                 680                 685

Phe Glu Tyr Leu Pro Arg Ala Tyr Gln Asn Gly Ala Asp Glu Leu Ala
            690                 695                 700

Arg Glu Lys Met His Asn Ala Ser Thr Ile Ala Gly Met Ala Phe Ala
705                 710                 715                 720

Asn Ala Phe Leu Gly Ile Asn His Ser Leu Ala His Lys Leu Gly Ala
                725                 730                 735

Glu Phe His Ile Pro His Gly Arg Ala Asn Thr Ile Leu Met Pro His
            740                 745                 750

Val Ile Arg Tyr Asn Ala Ala Lys Pro Lys Lys Phe Thr Ala Phe Pro
            755                 760                 765

Lys Tyr Glu Tyr Phe Lys Ala Asp Gln Arg Tyr Ala Glu Ile Ala Arg
    770                 775                 780

Met Leu Gly Leu Pro Ala Arg Thr Thr Glu Glu Gly Val Glu Ser Leu
785                 790                 795                 800

Val Gln Ala Ile Ile Lys Leu Ala Lys Gln Leu Asp Met Pro Leu Ser
                805                 810                 815

Ile Glu Ala Cys Gly Val Ser Lys Gln Glu Phe Glu Ser Lys Val Glu
            820                 825                 830

Lys Leu Ala Glu Leu Ala Phe Glu Asp Gln Cys Thr Thr Ala Asn Pro
            835                 840                 845

Lys Leu Pro Leu Val Ser Asp Leu Val His Ile Tyr Arg Gln Ala Phe
    850                 855                 860

Lys Gly Val
865

<210> SEQ ID NO 45
<211> LENGTH: 423
<212> TYPE: DNA
<213> ORGANISM: Geobacillus thermoglucosidans
<220> FEATURE:
<221> NAME/KEY: CDS
<222> LOCATION: (1)..(423)

<400> SEQUENCE: 45 gtg aga atc gcg ttg atc gcg cat gat aaa aag aaa gcg gat atg att    48
Val Arg Ile Ala Leu Ile Ala His Asp Lys Lys Lys Ala Asp Met Ile
1               5                   10                  15
```

```
gaa ttt gtg act gcc tat cag ccg att tta gaa caa cat gaa ctg tat      96
Glu Phe Val Thr Ala Tyr Gln Pro Ile Leu Glu Gln His Glu Leu Tyr
         20                  25                  30 gcg acg ggc acg acc ggc ttg cgc att cag gaa gcg aca gga ctg ccg     144
Ala Thr Gly Thr Thr Gly Leu Arg Ile Gln Glu Ala Thr Gly Leu Pro
         35                  40                  45 gtg cat cgc ttt caa tcg ggg cca tat ggc ggc gat caa gaa att ggt     192
Val His Arg Phe Gln Ser Gly Pro Tyr Gly Gly Asp Gln Glu Ile Gly
     50                  55                  60 gca atg att gcc cgc aat gaa atg gat atg gtg ata ttt ttc cgc gat     240
Ala Met Ile Ala Arg Asn Glu Met Asp Met Val Ile Phe Phe Arg Asp
65                  70                  75                  80 ccg ttg acg gca cag ccg cat gag ccg gat gtc agt gcg ctc att cgc     288
Pro Leu Thr Ala Gln Pro His Glu Pro Asp Val Ser Ala Leu Ile Arg
                 85                  90                  95 tta tgt gat gtc tat tcc gtg ccg ctt gca acc aat atg ggg acg gcg     336
Leu Cys Asp Val Tyr Ser Val Pro Leu Ala Thr Asn Met Gly Thr Ala
            100                 105                 110 gaa att tta att aaa ggg ctg gag cgc ggc gat ttt gcg tgg agg aat     384
Glu Ile Leu Ile Lys Gly Leu Glu Arg Gly Asp Phe Ala Trp Arg Asn
        115                 120                 125 att gtc cgc ggc cga aaa ggt gag aca aat gga ata taa                 423
Ile Val Arg Gly Arg Lys Gly Glu Thr Asn Gly Ile
    130                 135                 140

<210> SEQ ID NO 46
<211> LENGTH: 140
<212> TYPE: PRT
<213> ORGANISM: Geobacillus thermoglucosidans

<400> SEQUENCE: 46

Val Arg Ile Ala Leu Ile Ala His Asp Lys Lys Ala Asp Met Ile
1               5                   10                  15

Glu Phe Val Thr Ala Tyr Gln Pro Ile Leu Glu Gln His Glu Leu Tyr
         20                  25                  30

Ala Thr Gly Thr Thr Gly Leu Arg Ile Gln Glu Ala Thr Gly Leu Pro
         35                  40                  45

Val His Arg Phe Gln Ser Gly Pro Tyr Gly Gly Asp Gln Glu Ile Gly
     50                  55                  60

Ala Met Ile Ala Arg Asn Glu Met Asp Met Val Ile Phe Phe Arg Asp
65                  70                  75                  80

Pro Leu Thr Ala Gln Pro His Glu Pro Asp Val Ser Ala Leu Ile Arg
                 85                  90                  95

Leu Cys Asp Val Tyr Ser Val Pro Leu Ala Thr Asn Met Gly Thr Ala
            100                 105                 110

Glu Ile Leu Ile Lys Gly Leu Glu Arg Gly Asp Phe Ala Trp Arg Asn
        115                 120                 125

Ile Val Arg Gly Arg Lys Gly Glu Thr Asn Gly Ile
    130                 135                 140

<210> SEQ ID NO 47
<211> LENGTH: 960
<212> TYPE: DNA
<213> ORGANISM: Geobacillus thermoglucosidans
<220> FEATURE:
<221> NAME/KEY: CDS
<222> LOCATION: (1)..(960)

<400> SEQUENCE: 47 atg aaa caa caa ggc atg aat cga gta gca ctt ata gga acg ggg ttc      48
```

```
Met Lys Gln Gln Gly Met Asn Arg Val Ala Leu Ile Gly Thr Gly Phe
1               5                   10                  15 gtt ggg gcc agc tat gca ttt gcc ctt atg aac caa gga ata gca gat        96
Val Gly Ala Ser Tyr Ala Phe Ala Leu Met Asn Gln Gly Ile Ala Asp
            20                  25                  30 gag tta gta ttg att gat gta aat aag aat aag gca gag ggc gat gtg       144
Glu Leu Val Leu Ile Asp Val Asn Lys Asn Lys Ala Glu Gly Asp Val
                35                  40                  45 atg gat tta aat cac gga aaa gta ttc gcg ccg aag ccg atg aat att       192
Met Asp Leu Asn His Gly Lys Val Phe Ala Pro Lys Pro Met Asn Ile
 50                  55                  60 tgg ttt gga gat tat caa gat tgc caa gac gcc gat ttg gtg gtg att       240
Trp Phe Gly Asp Tyr Gln Asp Cys Gln Asp Ala Asp Leu Val Val Ile
 65                  70                  75                  80 tgt gca ggg gct aac caa aag ccg gga gaa aca aga ctg gat ctt gtt       288
Cys Ala Gly Ala Asn Gln Lys Pro Gly Glu Thr Arg Leu Asp Leu Val
                85                  90                  95 gac aaa aat att aat atc ttc aaa acg att gtc gat tct gtg atg aaa       336
Asp Lys Asn Ile Asn Ile Phe Lys Thr Ile Val Asp Ser Val Met Lys
                100                 105                 110 tcc gga ttt gat ggc gtt ttt ctt gtg gca acg aac cca gtg gat att       384
Ser Gly Phe Asp Gly Val Phe Leu Val Ala Thr Asn Pro Val Asp Ile
            115                 120                 125 tta acg tat gct act tgg aaa ttt agc ggg tta ccg aaa gag cgg gta       432
Leu Thr Tyr Ala Thr Trp Lys Phe Ser Gly Leu Pro Lys Glu Arg Val
130                 135                 140 atc ggc tca gga acg att ctt gat aca gca aga ttc cgc ttc ttg cta       480
Ile Gly Ser Gly Thr Ile Leu Asp Thr Ala Arg Phe Arg Phe Leu Leu
145                 150                 155                 160 agt gaa tat ttt caa gtg gct ccg acc aat gta cat gcg tat att att       528
Ser Glu Tyr Phe Gln Val Ala Pro Thr Asn Val His Ala Tyr Ile Ile
                165                 170                 175 ggc gag cat ggg gat aca gag ctg cct gtt tgg agc cat gcg gaa att       576
Gly Glu His Gly Asp Thr Glu Leu Pro Val Trp Ser His Ala Glu Ile
            180                 185                 190 gga agc att cca gtt gag caa ata ttg atg caa aac gat aac tat aga       624
Gly Ser Ile Pro Val Glu Gln Ile Leu Met Gln Asn Asp Asn Tyr Arg
        195                 200                 205 aaa gag gat tta gac aat atc ttt gtt aat gtt cgt gat gcg gca tat       672
Lys Glu Asp Leu Asp Asn Ile Phe Val Asn Val Arg Asp Ala Ala Tyr
210                 215                 220 caa atc att gag aaa aaa ggg gca acg tat tac ggc att gca atg gga       720
Gln Ile Ile Glu Lys Lys Gly Ala Thr Tyr Tyr Gly Ile Ala Met Gly
225                 230                 235                 240 tta gtc cgt atc act cgt gct att ttg cac aat gaa aat gcc atc tta       768
Leu Val Arg Ile Thr Arg Ala Ile Leu His Asn Glu Asn Ala Ile Leu
                245                 250                 255 acc gtt tct gct cat ttg gac ggc caa tat ggc gaa cga aat gtt tat       816
Thr Val Ser Ala His Leu Asp Gly Gln Tyr Gly Glu Arg Asn Val Tyr
            260                 265                 270 att ggc gtg cct gcc att atc aac cga aac ggt att cgt gaa gtg atg       864
Ile Gly Val Pro Ala Ile Ile Asn Arg Asn Gly Ile Arg Glu Val Met
        275                 280                 285 gaa ttg acg cta aat gaa aca gaa caa caa caa ttc cat cat agt gta       912
Glu Leu Thr Leu Asn Glu Thr Glu Gln Gln Gln Phe His His Ser Val
290                 295                 300 act gta tta aaa gac att ctt tcc cgt tat ttt gat gat gta aaa taa       960
Thr Val Leu Lys Asp Ile Leu Ser Arg Tyr Phe Asp Asp Val Lys
305                 310                 315
```

<210> SEQ ID NO 48
<211> LENGTH: 319
<212> TYPE: PRT
<213> ORGANISM: Geobacillus thermoglucosidans

<400> SEQUENCE: 48

Met Lys Gln Gln Gly Met Asn Arg Val Ala Leu Ile Gly Thr Gly Phe
1               5                   10                  15

Val Gly Ala Ser Tyr Ala Phe Ala Leu Met Asn Gln Gly Ile Ala Asp
            20                  25                  30

Glu Leu Val Leu Ile Asp Val Asn Lys Asn Lys Ala Glu Gly Asp Val
        35                  40                  45

Met Asp Leu Asn His Gly Lys Val Phe Ala Pro Lys Pro Met Asn Ile
50                  55                  60

Trp Phe Gly Asp Tyr Gln Asp Cys Gln Asp Ala Asp Leu Val Val Ile
65                  70                  75                  80

Cys Ala Gly Ala Asn Gln Lys Pro Gly Glu Thr Arg Leu Asp Leu Val
                85                  90                  95

Asp Lys Asn Ile Asn Ile Phe Lys Thr Ile Val Asp Ser Val Met Lys
            100                 105                 110

Ser Gly Phe Asp Gly Val Phe Leu Val Ala Thr Asn Pro Val Asp Ile
        115                 120                 125

Leu Thr Tyr Ala Thr Trp Lys Phe Ser Gly Leu Pro Lys Glu Arg Val
130                 135                 140

Ile Gly Ser Gly Thr Ile Leu Asp Thr Ala Arg Phe Arg Phe Leu Leu
145                 150                 155                 160

Ser Glu Tyr Phe Gln Val Ala Pro Thr Asn Val His Ala Tyr Ile Ile
                165                 170                 175

Gly Glu His Gly Asp Thr Glu Leu Pro Val Trp Ser His Ala Glu Ile
            180                 185                 190

Gly Ser Ile Pro Val Glu Gln Ile Leu Met Gln Asn Asp Asn Tyr Arg
        195                 200                 205

Lys Glu Asp Leu Asp Asn Ile Phe Val Asn Val Arg Asp Ala Ala Tyr
210                 215                 220

Gln Ile Ile Glu Lys Lys Gly Ala Thr Tyr Tyr Gly Ile Ala Met Gly
225                 230                 235                 240

Leu Val Arg Ile Thr Arg Ala Ile Leu His Asn Glu Asn Ala Ile Leu
                245                 250                 255

Thr Val Ser Ala His Leu Asp Gly Gln Tyr Gly Glu Arg Asn Val Tyr
            260                 265                 270

Ile Gly Val Pro Ala Ile Ile Asn Arg Asn Gly Ile Arg Glu Val Met
        275                 280                 285

Glu Leu Thr Leu Asn Glu Thr Glu Gln Gln Gln Phe His His Ser Val
290                 295                 300

Thr Val Leu Lys Asp Ile Leu Ser Arg Tyr Phe Asp Asp Val Lys
305                 310                 315

<210> SEQ ID NO 49
<211> LENGTH: 975
<212> TYPE: DNA
<213> ORGANISM: Geobacillus thermoglucosidans
<220> FEATURE:
<221> NAME/KEY: CDS
<222> LOCATION: (1)..(975)

<400> SEQUENCE: 49

```
gtg agc agt gat tta ttt tcg aca tta aaa gaa aaa ata gcg gga aaa         48
Val Ser Ser Asp Leu Phe Ser Thr Leu Lys Glu Lys Ile Ala Gly Lys
 1               5                  10                  15 caa cgg aaa atc gtg ttt ccg gaa ggg ctt gat gag cgt att tta aca         96
Gln Arg Lys Ile Val Phe Pro Glu Gly Leu Asp Glu Arg Ile Leu Thr
             20                  25                  30 gcg gta agc cgt ctg gcg aac gag caa atc gtc acg ccg att gtc att        144
Ala Val Ser Arg Leu Ala Asn Glu Gln Ile Val Thr Pro Ile Val Ile
         35                  40                  45 ggc aat gaa gaa gcg gtt aag caa aaa gca agc gag ctt ggg ctg acg        192
Gly Asn Glu Glu Ala Val Lys Gln Lys Ala Ser Glu Leu Gly Leu Thr
 50                  55                  60 ctt ccg aat gtc gaa atc att gat ccg cat cag tac ggg gaa atg gac        240
Leu Pro Asn Val Glu Ile Ile Asp Pro His Gln Tyr Gly Glu Met Asp
 65                  70                  75                  80 aag ctt gtt gcg gca ttt gtc gaa cgc cgc aaa ggg aaa gtg acg gaa        288
Lys Leu Val Ala Ala Phe Val Glu Arg Arg Lys Gly Lys Val Thr Glu
             85                  90                  95 gaa gcg gcg cgg aag ctg ctt ctt gac gaa aat tat ttt ggc acc atg        336
Glu Ala Ala Arg Lys Leu Leu Leu Asp Glu Asn Tyr Phe Gly Thr Met
        100                 105                 110 ctt gtg tac atg gat aag gcg cat ggg ctt gtc agc ggc gcg gcg cat        384
Leu Val Tyr Met Asp Lys Ala His Gly Leu Val Ser Gly Ala Ala His
        115                 120                 125 tcg acg gct gat acg gtg cgg cct gcg ttg caa att ata aaa acg aaa        432
Ser Thr Ala Asp Thr Val Arg Pro Ala Leu Gln Ile Ile Lys Thr Lys
130                 135                 140 caa ggc gtc cgc aaa acg tca gga gta ttc att atg gtg cgc ggt gat        480
Gln Gly Val Arg Lys Thr Ser Gly Val Phe Ile Met Val Arg Gly Asp
145                 150                 155                 160 gaa aag tac gtg ttt gcc gat tgc gcg atc aac att gcc ccg gac agc        528
Glu Lys Tyr Val Phe Ala Asp Cys Ala Ile Asn Ile Ala Pro Asp Ser
                165                 170                 175 caa gat ttg gcg gaa atc gct gtc gaa agc gcc aac acg gca aaa atg        576
Gln Asp Leu Ala Glu Ile Ala Val Glu Ser Ala Asn Thr Ala Lys Met
            180                 185                 190 ttc gac att gag ccg cgc gtg gcg atg ttg agc ttt tcg aca aaa gga        624
Phe Asp Ile Glu Pro Arg Val Ala Met Leu Ser Phe Ser Thr Lys Gly
        195                 200                 205 tca gcg aaa tcg cca gaa acg gaa aaa gtc gtc gaa gcg gtg cgg ctt        672
Ser Ala Lys Ser Pro Glu Thr Glu Lys Val Val Glu Ala Val Arg Leu
210                 215                 220 gcg aaa gaa atg gcg cct gac tta gtg ctg gac ggt gag ttt cag ttc        720
Ala Lys Glu Met Ala Pro Asp Leu Val Leu Asp Gly Glu Phe Gln Phe
225                 230                 235                 240 gac gcg gcg ttt gtt ccg tct gtc gcg aaa aag aaa gcg cca gat tcc        768
Asp Ala Ala Phe Val Pro Ser Val Ala Lys Lys Lys Ala Pro Asp Ser
                245                 250                 255 gtc att caa gga gac gcg aac gta ttt att ttc cca agc ctt gaa gcg        816
Val Ile Gln Gly Asp Ala Asn Val Phe Ile Phe Pro Ser Leu Glu Ala
            260                 265                 270 gga aat atc ggc tat aaa atc gcc cag cgt ctc ggc aac ttt gaa gcg        864
Gly Asn Ile Gly Tyr Lys Ile Ala Gln Arg Leu Gly Asn Phe Glu Ala
        275                 280                 285 gtc ggc ccg att ttg caa gga ctc aat aag cct gtg aac gac ctg tca        912
Val Gly Pro Ile Leu Gln Gly Leu Asn Lys Pro Val Asn Asp Leu Ser
        290                 295                 300 cgc ggt tgc aat gcg gaa gat gtg tac aag ctg acg ctt ata act gcg        960
Arg Gly Cys Asn Ala Glu Asp Val Tyr Lys Leu Thr Leu Ile Thr Ala
305                 310                 315                 320
```

```
gcg caa tcg cta taa                                              975
Ala Gln Ser Leu <210> SEQ ID NO 50
<211> LENGTH: 324
<212> TYPE: PRT
<213> ORGANISM: Geobacillus thermoglucosidans

<400> SEQUENCE: 50

Val Ser Ser Asp Leu Phe Ser Thr Leu Lys Glu Lys Ile Ala Gly Lys
1               5                   10                  15

Gln Arg Lys Ile Val Phe Pro Glu Gly Leu Asp Glu Arg Ile Leu Thr
            20                  25                  30

Ala Val Ser Arg Leu Ala Asn Glu Gln Ile Val Thr Pro Ile Val Ile
        35                  40                  45

Gly Asn Glu Glu Ala Val Lys Gln Lys Ala Ser Glu Leu Gly Leu Thr
    50                  55                  60

Leu Pro Asn Val Glu Ile Ile Asp Pro His Gln Tyr Gly Glu Met Asp
65                  70                  75                  80

Lys Leu Val Ala Ala Phe Val Glu Arg Arg Lys Gly Lys Val Thr Glu
                85                  90                  95

Glu Ala Ala Arg Lys Leu Leu Leu Asp Glu Asn Tyr Phe Gly Thr Met
            100                 105                 110

Leu Val Tyr Met Asp Lys Ala His Gly Leu Val Ser Gly Ala Ala His
        115                 120                 125

Ser Thr Ala Asp Thr Val Arg Pro Ala Leu Gln Ile Ile Lys Thr Lys
130                 135                 140

Gln Gly Val Arg Lys Thr Ser Gly Val Phe Ile Met Val Arg Gly Asp
145                 150                 155                 160

Glu Lys Tyr Val Phe Ala Asp Cys Ala Ile Asn Ile Ala Pro Asp Ser
                165                 170                 175

Gln Asp Leu Ala Glu Ile Ala Val Glu Ser Ala Asn Thr Ala Lys Met
            180                 185                 190

Phe Asp Ile Glu Pro Arg Val Ala Met Leu Ser Phe Ser Thr Lys Gly
        195                 200                 205

Ser Ala Lys Ser Pro Glu Thr Glu Lys Val Val Glu Ala Val Arg Leu
    210                 215                 220

Ala Lys Glu Met Ala Pro Asp Leu Val Leu Asp Gly Glu Phe Gln Phe
225                 230                 235                 240

Asp Ala Ala Phe Val Pro Ser Val Ala Lys Lys Lys Ala Pro Asp Ser
                245                 250                 255

Val Ile Gln Gly Asp Ala Asn Val Phe Ile Phe Pro Ser Leu Glu Ala
            260                 265                 270

Gly Asn Ile Gly Tyr Lys Ile Ala Gln Arg Leu Gly Asn Phe Glu Ala
        275                 280                 285

Val Gly Pro Ile Leu Gln Gly Leu Asn Lys Pro Val Asn Asp Leu Ser
    290                 295                 300

Arg Gly Cys Asn Ala Glu Asp Val Tyr Lys Leu Thr Leu Ile Thr Ala
305                 310                 315                 320

Ala Gln Ser Leu

<210> SEQ ID NO 51
<211> LENGTH: 750
<212> TYPE: DNA
<213> ORGANISM: Geobacillus thermoglucosidans
```

<220> FEATURE:
<221> NAME/KEY: CDS
<222> LOCATION: (1)..(750)

<400> SEQUENCE: 51

```
atg gat gtc gat gtc aag cga gat cag acg ctg tta aaa gat cat gag    48
Met Asp Val Asp Val Lys Arg Asp Gln Thr Leu Leu Lys Asp His Glu
1               5                   10                  15 atg aaa aag ctt att cgc cgc agc caa gag ggg gac caa cag gcg cgc    96
Met Lys Lys Leu Ile Arg Arg Ser Gln Glu Gly Asp Gln Gln Ala Arg
            20                  25                  30 aat gaa att atc caa aaa aac atg cgc ctc gtt tgg tcg gtc gtc cag   144
Asn Glu Ile Ile Gln Lys Asn Met Arg Leu Val Trp Ser Val Val Gln
        35                  40                  45 cgc ttt ttg aac cgc gga tac gag ccg gac gat tta ttt caa att ggc   192
Arg Phe Leu Asn Arg Gly Tyr Glu Pro Asp Asp Leu Phe Gln Ile Gly
    50                  55                  60 tgc atc ggc ttg ctt aaa tct gtt gat aag ttt gat ttg tcg tat gac   240
Cys Ile Gly Leu Leu Lys Ser Val Asp Lys Phe Asp Leu Ser Tyr Asp
65                  70                  75                  80 gtg aag ttt tcc aca tat gcg gtg ccg atg atc atc ggc gaa att cag   288
Val Lys Phe Ser Thr Tyr Ala Val Pro Met Ile Ile Gly Glu Ile Gln
                85                  90                  95 cgg ttt atc cgc gat gac ggg acg gtg aaa gtg agc cgt tcc tta aaa   336
Arg Phe Ile Arg Asp Asp Gly Thr Val Lys Val Ser Arg Ser Leu Lys
            100                 105                 110 gaa acg ggc aat aaa atc cgg aaa gca aga gac gag ctt tcg aaa aaa   384
Glu Thr Gly Asn Lys Ile Arg Lys Ala Arg Asp Glu Leu Ser Lys Lys
        115                 120                 125 cat gga cgg gcg cca acg gtg aca gaa atc gcc gat tat tta gaa att   432
His Gly Arg Ala Pro Thr Val Thr Glu Ile Ala Asp Tyr Leu Glu Ile
    130                 135                 140 tct cca gaa gaa gtg gtg ctt gcc cag gaa gcc gtt cgt tcc ccg gct   480
Ser Pro Glu Glu Val Val Leu Ala Gln Glu Ala Val Arg Ser Pro Ala
145                 150                 155                 160 tcc att cac gaa aca gtg tat gaa aac gac ggc gac ccg atc acg ctc   528
Ser Ile His Glu Thr Val Tyr Glu Asn Asp Gly Asp Pro Ile Thr Leu
                165                 170                 175 ctc gat caa att gct gat gcc gac gaa gca tca tgg ttt gat aaa atc   576
Leu Asp Gln Ile Ala Asp Ala Asp Glu Ala Ser Trp Phe Asp Lys Ile
            180                 185                 190 gcg ttg aaa aaa gcg att gag gag ctg gat gaa cgg gaa cgt ctc atc   624
Ala Leu Lys Lys Ala Ile Glu Glu Leu Asp Glu Arg Glu Arg Leu Ile
        195                 200                 205 gtc tat ttg cgt tat tac aaa gat caa acc cag tcg gaa gtg gca tca   672
Val Tyr Leu Arg Tyr Tyr Lys Asp Gln Thr Gln Ser Glu Val Ala Ser
    210                 215                 220 aga tta ggc atc tct caa gtt caa gta tcc cgt ctt gaa aaa aaa att   720
Arg Leu Gly Ile Ser Gln Val Gln Val Ser Arg Leu Glu Lys Lys Ile
225                 230                 235                 240 tta cag caa ata aag gag aga atg gat ggg                           750
Leu Gln Gln Ile Lys Glu Arg Met Asp Gly
                245                 250
```

<210> SEQ ID NO 52
<211> LENGTH: 250
<212> TYPE: PRT
<213> ORGANISM: Geobacillus thermoglucosidans

<400> SEQUENCE: 52

Met Asp Val Asp Val Lys Arg Asp Gln Thr Leu Leu Lys Asp His Glu

```
  1               5                   10                  15
Met Lys Lys Leu Ile Arg Arg Ser Gln Glu Gly Asp Gln Gln Ala Arg
              20                  25                  30
Asn Glu Ile Ile Gln Lys Asn Met Arg Leu Val Trp Ser Val Val Gln
              35                  40                  45
Arg Phe Leu Asn Arg Gly Tyr Glu Pro Asp Asp Leu Phe Gln Ile Gly
 50                  55                  60
Cys Ile Gly Leu Leu Lys Ser Val Asp Lys Phe Asp Leu Ser Tyr Asp
 65                  70                  75                  80
Val Lys Phe Ser Thr Tyr Ala Val Pro Met Ile Ile Gly Glu Ile Gln
                 85                  90                  95
Arg Phe Ile Arg Asp Asp Gly Thr Val Lys Val Ser Arg Ser Leu Lys
                100                 105                 110
Glu Thr Gly Asn Lys Ile Arg Lys Ala Arg Asp Glu Leu Ser Lys Lys
                115                 120                 125
His Gly Arg Ala Pro Thr Val Thr Glu Ile Ala Asp Tyr Leu Glu Ile
                130                 135                 140
Ser Pro Glu Glu Val Val Leu Ala Gln Glu Ala Val Arg Ser Pro Ala
145                 150                 155                 160
Ser Ile His Glu Thr Val Tyr Glu Asn Asp Gly Asp Pro Ile Thr Leu
                165                 170                 175
Leu Asp Gln Ile Ala Asp Ala Asp Glu Ala Ser Trp Phe Asp Lys Ile
                180                 185                 190
Ala Leu Lys Lys Ala Ile Glu Glu Leu Asp Glu Arg Glu Arg Leu Ile
                195                 200                 205
Val Tyr Leu Arg Tyr Tyr Lys Asp Gln Thr Gln Ser Glu Val Ala Ser
                210                 215                 220
Arg Leu Gly Ile Ser Gln Val Gln Val Ser Arg Leu Glu Lys Lys Ile
225                 230                 235                 240
Leu Gln Gln Ile Lys Glu Arg Met Asp Gly
                245                 250
```

<210> SEQ ID NO 53
<211> LENGTH: 29
<212> TYPE: DNA
<213> ORGANISM: Artificial Sequence
<220> FEATURE:
<223> OTHER INFORMATION: Synthetic primer

<400> SEQUENCE: 53
ctgcaagctt tggcagacaa cggcatcac                                    29

<210> SEQ ID NO 54
<211> LENGTH: 29
<212> TYPE: DNA
<213> ORGANISM: Artificial Sequence
<220> FEATURE:
<223> OTHER INFORMATION: Synthetic primer

<400> SEQUENCE: 54
ttgcgtaacc gaagaccttg cctgagtcc                                    29

<210> SEQ ID NO 55
<211> LENGTH: 33
<212> TYPE: DNA
<213> ORGANISM: Artificial Sequence
<220> FEATURE:
<223> OTHER INFORMATION: Synthetic primer

```
<400> SEQUENCE: 55
cctcgagcgg caaacagagc tttaaaacca ggc                                 33

<210> SEQ ID NO 56
<211> LENGTH: 33
<212> TYPE: DNA
<213> ORGANISM: Artificial Sequence
<220> FEATURE:
<223> OTHER INFORMATION: Synthetic primer

<400> SEQUENCE: 56
gggtctagag ccgcttcgtt ttccaactga tgc                                 33

<210> SEQ ID NO 57
<211> LENGTH: 22
<212> TYPE: DNA
<213> ORGANISM: Artificial Sequence
<220> FEATURE:
<223> OTHER INFORMATION: Synthetic primer

<400> SEQUENCE: 57
tctttcgctt ccagggctgt tc                                             22

<210> SEQ ID NO 58
<211> LENGTH: 43
<212> TYPE: DNA
<213> ORGANISM: Artificial Sequence
<220> FEATURE:
<223> OTHER INFORMATION: Synthetic primer

<400> SEQUENCE: 58
gcgcggagct cgtcgacctg actttgaata caacaaggtg aac                      43
```